(12) United States Patent
Akpo et al.

(10) Patent No.: US 10,793,919 B2
(45) Date of Patent: *Oct. 6, 2020

(54) METHODS FOR DETERMINING FITNESS IN PLANTS

(71) Applicant: BASF SE, Ludwigshafen am Rhein (DE)

(72) Inventors: Esse Ifebi Herve Akpo, Ghent (BE); Benjamin Laga, Wingene (BE); Marc De Block, Merelbeke (BE)

(73) Assignee: BASF SE, Ludwigshafen am Rhein (DE)

( * ) Notice: Subject to any disclaimer, the term of this patent is extended or adjusted under 35 U.S.C. 154(b) by 136 days.

This patent is subject to a terminal disclaimer.

(21) Appl. No.: 15/919,141

(22) Filed: Mar. 12, 2018

(65) Prior Publication Data

US 2018/0209000 A1    Jul. 26, 2018

Related U.S. Application Data

(63) Continuation of application No. 13/703,037, filed as application No. PCT/EP2011/003052 on Jun. 15, 2011, now Pat. No. 9,914,981.

(60) Provisional application No. 61/355,825, filed on Jun. 17, 2010.

(30) Foreign Application Priority Data

Jun. 18, 2010 (EP) ..................................... 10075262

(51) Int. Cl.
| | | |
|---|---|---|
| *A01H 1/04* | (2006.01) | |
| *A01H 5/00* | (2018.01) | |
| *C12Q 1/6895* | (2018.01) | |
| *A01G 22/00* | (2018.01) | |

(52) U.S. Cl.
CPC ........... *C12Q 1/6895* (2013.01); *A01G 22/00* (2018.02); *A01H 1/04* (2013.01); *A01H 5/00* (2013.01); *C12Q 2600/154* (2013.01); *Y02A 40/14* (2018.01)

(58) Field of Classification Search
CPC ........... C12Q 1/6895; A01H 1/04; A01H 5/00
See application file for complete search history.

(56) References Cited

U.S. PATENT DOCUMENTS 6,444,469 B1    9/2002    Dellaporta et al.

FOREIGN PATENT DOCUMENTS

| EP | 09075284 | 7/2009 |
| WO | 011000466 | 1/2001 |
| WO | 02066972 | 8/2002 |

OTHER PUBLICATIONS

Salmon, Armel, et al. "Brassica oleracea displays a high level of DNA methylation polymorphism." Plant Science 174.1 (2008): 61-70. (Year: 2008).*
Xiong, L. Z., et al. "Patterns of cytosine methylation in an elite rice hybrid and its parental lines, detected by a methylation-sensitive amplification polymorphism technique." Molecular and General Genetics MGG 261.3 (1999): 439-446. (Year: 1999).*
Boyko, Alex, et al., Transgenerational Adaptation of *Arabidopsis* to Stress Requires DNA Methylation and the Function of Dicer-Like Proteins, PLoS One, Mar. 2010, vol. 5, Issue 3; e9514.
Chinnusamy, Viswanathan, et al., Epigenetic Regulation of stress responses in plants, Current Opinion in Plant Biology, 2009, pp. 133-139, vol. 12.
De Block, Marc, et al., A simple and robust in vitro assay to quantify the vigour of oilseed rape lines and hybrids, Plant Physiol, Biochem, 2002, pp. 845-852, vol. 40.
Gehring, Mary, et al., DNA demethylation by DNA repair, Trends in Genetics, Jan. 2009, pp. 82-90, vol. 25.
Hauben, Miriam, et al., Energy use efficiency is characterized by an epigenetic component that can be directed through artificial selection to increase yield, Proc Natl Acad Sci USA, Nov. 24, 2009, pp. 20109-20114, vol. 106, No. 47.
Jablonka, Eva, et al., Transgenerational Epigenetic Inheritance: Prevalence, Mechanisms, and Implications for the Study of Heredity and Evolution, The Quarterly Review of Biology, Jun. 2009, pp. 131-176, vol. 84, No. 2.
Juszczuk, Izabela, et al., Effect of Mitochondrial genome rearrangement on respiratory activity, photosynthesis, photorespiration and energy status of MSC16 cucumber (*Cucumis sativus*) mutant, Physiol. Plant, 2007, pp. 527-541, vol. 131.
Kraus, Edwin, et al., Yield advantage of a slow over a fast respiring population of *Lolium perenne* cv. S23 depends on plant density, New Phytol., 1993, pp. 39-44, vol. 123.
Kraus, Edwin, et al., The effect of handling on the yield of two populations of Lolium perenne selected for differences in mature leaf respiration rate, Physiologia Plantarium, 1993, pp. 341-346, vol. 89.
Fonseca Lira-Medeiros, Catarina, et al., Epigenetic Variation in Mangrove Plants Occurring in Contrasting Natural Environment, Plos One, Apr. 2010, vol. 5, Issue 4, e10326.
Lukens, Lewis N., et al., The plant genome's methylation status and response to stress: implications for plant improvement, Current Opinion in Plant Biology, 2007, pp. 317-322, vol. 10.
Matthies, M., et al., Variation in oil palm (*Elaeis guineensis* Jacq.) tissue culture-derived regenerants revealed by AFLPs with methylation-sensitive enzymes, Theor App. Genet, 2001. p. 971-979, vol. 102.
Molinier, Jean, et al., Transgeneration memory of stress in plants, Nature Publishing Group, Aug. 2006, pp. 1046-1049, vol. 442.
Nunes-Nesi, Adriano, et al., Enhanced Photosynthetic Performance and Growth as a Consequence of Decreasing Mitochondrial Malate Dehydrogenase Activity in Transgenic Tomato Plants, Plant Physiology, Feb. 2005, pp. 611-622, vol. 137.

(Continued)

*Primary Examiner* — Weihua Fan
(74) *Attorney, Agent, or Firm* — Arent Fox LLP

(57) ABSTRACT

Means and methods are provided to produce abiotic stress tolerant plants with improved yield based on the specific identification of a DNA methylation signature in the plants out of a population of the plants. The methods involve identification and utilization of epigenetic features of a plant with high energy use efficiency.

9 Claims, 6 Drawing Sheets

Specification includes a Sequence Listing.

(56) References Cited

OTHER PUBLICATIONS

Urano, Kaoru, et al., Omics analyses of regulatory networks in plant abiotic stress responses, Current Opinion in Plant Biology, 2010, pp. 132-138, vol. 13.
Vuylsteke Marnik, et al., AFLP-based transcript profiling (cDNA-AFLP) for genome-wide expression analysis, Nature Protocols, 2007, pp. 1399-1413, vol. 2(6).
Wilson, D., Response to Selection for Dark Respiration Rate of Mature Leaves in Lolium perenne and its Effects on Growth of Young Plants and Simulated Swards, Annals of Botany Company, 1982, pp. 303-312, vol. 49.
Wilson, D., et al., Effect of Selection for Dark Respiration Rate of Mature Leaves on Crop Yields of *Lolium perenne* cv. S23, Annals of Botany Company, 1982, pp. 313-320, vol. 49.
Zhang, Xiaoyu, et al., Genome-wide High-Resolution Mapping and Functional Analysis of DNA Methylation in *Arabidopsis*, Cell 126, Sep. 22, 2006, pp. 1189-1201.
Lobell, David B., et al., Crop yield gaps: their importance, magnitudes, and causes, Annual Review of Environment and Resources, 34.1 (2009): 179.
Mittler, Ron, Abiotic stress, the field environment and stress combination, Trends in Plant Science, 11.1, (2006): 15-19.
Blum, A., Drought resistance, water-use efficiency, and yield potential-are they compatible, dissonant, or mutually exclusive?, Crop and Pasture Science 56.11, (2005): 11-59-1168.
Springer, Nathan M., Epigenetics and Crop improvement, Trends in Genetics 29.4 (2013): 241-247.
Xiong, L.Z., et al., Patterns of cytosine methylation in an elite rice hybrid and its parental lines, detected by a methylation-sensitive amplication polymorphism technique, Molecular and General Genetics MGG 261.3 (1999): 439-446.
Ying, Jifeng, et al., Comparison of high-yield rice in tropical and subtropical environments: I. Determinants of grain and dry matter yields, Field Crops Research 57.1 (1998): 71-84.
Virmani, S., et al., Heterosis breeding in rice (*Oryza sativa* L.), Theoretical and Applied Genetics 63.4 (1982):373-380.
Lister, Ryan, et al., Finding the fifth base: genome-wide sequencing of cytosine methylation, Genome Research 19.6 (2009): 959-966.
Salmon, Armel, et al. Brassica oleracea displays a high level of DNA methylation polymorphism, Plant Science 174.1 (2008): 61-70.
Zhao, Jianyi, et al., Conditional QTL mapping of oil content in rapeseed with respect to protein content and traits related to plant development and grain yield, Theoretical and Applied Genetics 113.1 (2006): 33-38.
Jun, Zou, et al., Broadening the avenue of intersubgenomic heterosis in oilseed Brassica, TAG Theoretical and Applied Genetics. vol. 120. No. 2. Springer-Verlag GmbH, 2010, published online on Nov. 13, 2009.
Dixon, G.R., 2007. Chapter 1, Origins and diversity of Brassica and its relatives, in: Vegetable Brassicas and Related Crucifers, ISBN 0851993958. DOI 10.1079/9780851993959.0001.

\* cited by examiner

A

B

METHODS FOR DETERMINING FITNESS IN PLANTS

CROSS-REFERENCE TO RELATED APPLICATIONS

This application is a continuation of U.S. patent application Ser. No. 13/703,037, filed Dec. 10, 2012, which claims the benefit of PCT International Application No. PCT/EP2011/003052, filed Jun. 15, 2011, which claims the benefit of European Patent Application Serial No. 10075262.5, filed Jun. 18, 2010, and U.S. Patent Application Ser. No. 61/355,825, filed Jun. 17, 2010, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "bcs102011.txt", created on Dec. 7, 2012, and having a size of 8,000 bytes and is filed concurrently with the specification. The sequence listing contained in this ASCII formatted document is part of the specification and is herein incorporated by reference in its entirety.

FIELD OF THE INVENTION

The invention relates to the field of agriculture more particularly to the field of molecular breeding. The invention provides methods to select (sub)populations of plants, including crop plants, exhibiting a high energy use efficiency, based on their epigenetic profile, more specifically their DNA methylation profile. Also provided are plants and populations of plants exhibiting high energy use efficiency, which may be identified by their epigenetic features.

BACKGROUND OF THE INVENTION

The production of agricultural goods and in particular food and feed production, in sufficient quantity and quality is an increasingly challenging task. One the one hand, there is a continuous growth of the demand for agricultural products, due to increase in world population as well as increase in the average standard of living for large parts of the world population. On the other hand, the area suitable or available for agriculture is continuously shrinking, partly because of changing climate conditions which can result in deterioration of areas previously suitable for agriculture. A continuous demand exists to increase the yield potential of agricultural crops, or at least maintaining such yield potential when growing agricultural crops under suboptimal or adverse abiotic conditions.

Up to now, efforts to increase the intrinsic yield potential have mainly focused on exploiting the genetic variability within the crops. By traditional breeding techniques existing or induced variant alleles are shuffled into new combinations. More recently, the pool of variability has been expanded through molecular techniques allowing the exchange of genetic material across species, and even kingdom, barriers.

However, much less attention has been devoted to the role epigenetic control mechanisms may play in determining quantitative traits such as yield. Indeed, all quantitative traits such as size and weights in animals or yield, particularly seed yield in crops exhibit variability with a normal distribution, even within a population of genetically identical individuals. Underlying the observed phenotypic variability are genetic components, environmental factors but also epigenetic components. The importance in plants of epigenetic control components in short and long term adaptation to stress has been documented (Molinier et al. 2006, Transgeneration memory of stress in plants. Nature 442, 1046-1049). Furthermore, it has been demonstrated that altered epigenetic states can be transmitted to successive generations that have not been or are no longer exposed to the inducing trigger (also reviewed in Jablonka and Raz, 2009 Transgenerational epigenetic inheritance: prevalence, mechanisms, and implications for the study of heredity and evolution. The Quarterly Review of Biology 84, No. 2, 131-176).

Various parameters have been employed to establish a correlation with the yield potential of a plant. A positive correlation has been found between yield potential and lower cellular respiration rates. Wilson described the response to selection of dark respiration rate of mature leaves in *Lolium perenne* and its effects on growth of young plants and simulated swards. (Wilson Ann. Bot. 49, 303-312 (1982)). Wilson and Jones described the effect of selection for dark respiration rate of mature leaves on crop yields of *Lolium perenne* cv. S23. (Wilson and Jones Ann. Bot. 49, 313-320 (1982)). Kraus et al. reported on the yield advantage of a 'slow-'over a 'fast-'respiring population of *Lolium perenne* cv. S23 which depends on plant density. (Kraus et al. New Phytol. 123, 39-44 (1993)) and on the effect of handling on the yield of two populations of *Lolium perenne* selected for differences in mature leaf respiration rate (Kraus et al. Physiol. Plant. 89, 341-346 (1993)). Nunes-Nesi et al. described enhanced photosynthetic performance and growth as a consequence of decreasing mitochondrial malate dehydrogenase activity in transgenic tomato plants. (Nunes-Nesi et al. Plant Physiol. 137, 611-622 (2005)). Juczczuk et al. reported on the effect of mitochondrial genome rearrangement on respiratory activity, photosynthesis, photorespiration and energy status of MSC16 cucumber (*Cucumis sativus*) mutant. (Juczczuk et al, Physiol. Plant. 131, 527-541 (2007)).

De Block and De Brouwer described a simple and robust in vitro assay to quantify the vigour of oilseed rape lines and hybrids. (Plant Physiol. Biochem. 40, 845-852 (2002)). WO02/066972 provides methods and means for determining parent inbred plant lines with good combining ability, for determining good combinations of parent inbred plant lines capable of yielding hybrid lines with high heterosis, and further for determining the agronomical performance of different plant lines, which can be performed in vitro by determining the electron flow in the mitochondria under control and stress conditions.

U.S. Pat. No. 6,444,469 describes methods of increasing or decreasing the rate of development of a plant by either increasing or decreasing the amount of methylated DNA found in the plant. The invention further provides plants that have been altered such that their rate of maturation is either increased or decreased relative to the rate of maturation of a non-altered plant.

Lira-Medeiros et al. (PLoS One, 2010 Apr. 26; 5(4): e10326) disclose that individuals with similar genetic profiles presented divergent epigenetic profiles that were characteristic of the population in a particular environment. It was found that of two morphologically different but genetically similar populations of mangrove plants from two different habitats, the population growing near a salt march displayed a hypomethylation of their genomic DNA when compared to plants growing at a riverside.

Boyko et al., (PLoS One. 2010 Mar. 3; 5(3):e9514) show that exposure of *Arabidopsis* plants to stresses, including salt, UVC, cold, heat and flood, resulted in a higher homologous recombination frequency, increased global genome methylation, and higher tolerance to stress in the untreated progeny. This transgenerational effect did not, however, persist in successive generations. Treatment of the progeny of stressed plants with 5-azacytidine was shown to decrease global genomic methylation and enhance stress tolerance.

Hauben et al. (2009, Proc Natl Acad Sci USA., 106: p20109-14.), demonstrated that, starting from an isogenic canola population, it was possible to generate through recurrent selection populations with distinct physiological and agronomical characteristics such as yield, energy use efficiency and abiotic stress tolerance, and that those populations were genetically identical but epigenetically different. It was furthermore found that both the DNA methylation patterns as well as the agronomical and physiological characteristics of the selected lines were heritable and that hybrids derived from parent lines selected for high energy use efficiencies had a 5% yield increase on top of heterosis. But although each of the selected lines was characterized by a specific epigenetic profile (histone modifications and global DNA methylation), taken together, the epigenetic characteristics did not reflect the physiological properties of the lines.

Thus, none of the prior art documents describe that specific epigenetic profiles can be linked to particular agronomical characteristics such as energy use efficiency, yield and tolerance to adverse abiotic conditions. The present invention discloses that particular changes in DNA methylation status during development correlate to the plant's vigor and gene expression and as such these features can be used to select (sub)populations of plants which have a higher yield potential and tolerance to adverse abiotic conditions. This problem is solved as herein after described in the different embodiments, examples and claims.

SUMMARY OF THE INVENTION

The invention relates to methods of finding a DNA methylation profile (or a DNA methylation signature which is equivalent wording) for a plant with a high energy use efficiency. In one embodiment the invention enables the artisan to correlate the DNA methylation profile with a plant with a high energy use efficiency.

In one embodiment the invention provides for a method to produce of a plant with a high energy use efficiency from a collection of plants from the same species or variety comprising the steps of a) providing a population consisting of a plurality of individual plants; b) obtaining a genomic DNA sample from individual plants of said collection/population at least a first and a second developmental stage in a manner which allows further cultivation of said sampled individual plants; c) determining of each of said individual plants the methylation profile of said genomic DNA obtained at said at least two stages; d) determining the epigenetic features of each of said individual plants by evaluating the changes in DNA methylation profile between said first and said second stage and e) identifying and selecting at least one plant which has a high relative occurrence of epigenetic features characteristic for high energy use efficiency when compared to other plants of said population, wherein said epigenetic features are selected from: i) gain and/or loss of methylated cytosines, preferably of mCG, mCHG and/or mCHH; and/or ii) no changes in C, preferably of CG, CHG and/or CHH.

In another embodiment the selected at least one plant has a high relative occurrence of at least five epigenetic features that are characteristic for high energy use efficiency when compared to other plants of said population, wherein said epigenetic features are selected from the group consisting of: no change in CTT-, mCTT-gain, no change in CCG, no change in CG, mCTC-gain, mCG-gain, mCTG-loss, mCTT-loss and mCCG-loss.

In yet another embodiment the epigenetic features of said at least one plant are selected from the group consisting of mCTC-gain, mCTG-loss, mCTT-loss, and mCCG-loss.

In a specific embodiment at least eight epigenetic features are present in the high energy use efficient plant when compared to other plants of said population.

In another specific embodiment said at least one high energy use efficient plant has a high relative occurrence of mCGG-loss when compared to other plants of said population.

In a further embodiment, when the epigenetic features have been determined based on markers that are polymorphic at said first stage, at least one plant has a high relative occurrence of at least 4 epigenetic features that are characteristic for high energy use efficiency when compared to other plants of said population, wherein said epigenetic features characteristic for high energy use efficiency are selected from mCTG-loss, mCG-gain, mCTA-loss, no change in CCG-mCCG, mCTC-gain, mCTT-gain, no change in CTC-mCTC or mCTG-gain.

In an even further embodiment the at least four features are selected from mCTG-loss, mCG-gain, mCTA-loss, no change in CCG-mCCG, mCTC-gain or mCTT-gain.

In alternative embodiments, high EUE plant can be produced by selecting for a low relative occurrence of epigenetic features that are characteristic for low EUE as described herein.

In a specific embodiment the first stage is the cotyledon and the second stage is the 3th leaf stage.

In another specific embodiment the plurality of individual plants consists of plants which are genetically uniform.

In a specific embodiment the methylation profile is determined by methylation sensitive AFLP.

In another specific embodiment the plant is a *Brassica*, rice, wheat or tomato plant.

In another specific embodiment the at least one produced high energy use efficient plant is further crossed with another plant.

In another embodiment the invention provides for a method for increasing harvest yield comprising the steps of a) providing a population of plants or seeds which are high energy use efficient; b) growing said plants or seeds in a field; c) producing a harvest from said plants or seeds.

In another embodiment the invention provides for a plant, seed or population of plants, obtained by any one of the methods described herein before.

In a specific embodiment the invention provides for a differential DNA methylation profile, characterized in that at least five epigenetic features characteristic for high energy use efficiency are detected in the genomic DNA of a plant between a first and a second developmental stage said plant, wherein said epigenetic features are selected from a) a gain and/or loss of methylated cytosines, preferably of mCG, mCHG and/or mCHH; and/or b) no changes in unmethylated cytosines, preferably of CG, CHG and/or CHH.

In a specific embodiment the differential DNA methylation profile is used to carry out any of the methods of the invention.

In another specific embodiment the invention provides for a method for obtaining a biological or chemical compound which is capable of generating a plant with a high energy use efficiency from a collection of plants form the same species or variety comprising the steps of a) providing a population consisting of a plurality of individual plants, b) subjecting said population of plants with a biological or chemical compound, c) obtaining a genomic DNA sample from individual plants of said collection/population at least a first and a second developmental stage in a manner which allows further cultivation of said sampled individual plants; d) determining of each of said individual plants the methylation profile of said genomic DNA obtained at said at least two stages; e) determining the epigenetic features of each of said individual plants by evaluating the changes in DNA methylation profile between said first and said second stage, wherein the presence of epigenetic features in the methylation profile as defined herein before is indicative for a biological compound capable of generating a plant with a high energy use efficiency.

GENERAL DEFINITIONS

Figure 1:
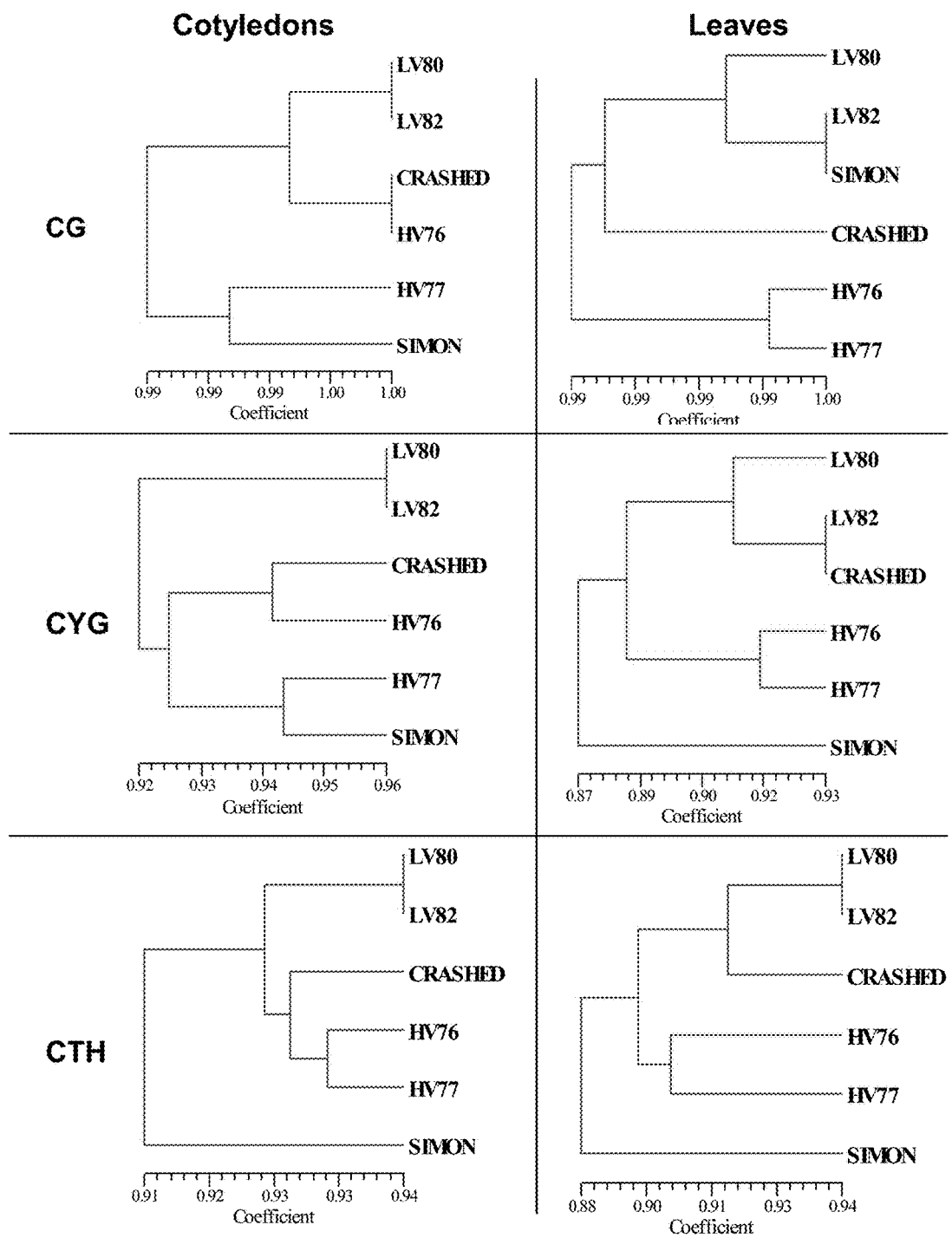
FIG. 1: Hierarchical clustering of the selected lines at the epigenetic level. (Coefficient=similarity coefficient).

As used herein "epigenetic, refers to factors such as histone variants, histone post-translational modification and DNA methylation. These epigenetic factors act in concert to regulate gene expression, giving rise to the so-called epigenome. Epigenetic changes do not alter the genome sequence, but can modify gene expression and phenotypes and can also be transmitted to following generations. Epigenetic regulation allows an organism to adapt to changes in the environment and is thus believed to play an important role in modulating response to stress, especially in plants which cannot escape their environment. Thus, together with genetic and environmental factors, epigenetic information determines the variability of a quantitative trait.

An epigenetic marker, as used herein, refers to a specific epigenetic modification (e.g. DNA methylation or histone modification) at a particular site in the genome. Polyploid organisms such as plants, can be monomorphic for a particular epigenetic marker, i.e. on each chromosomal copy, the same modification occurs at that particular site (locus), but can also be polymorphic, i.e. different epigenetic modifications are present on the two or more chromosomal copies at that site (locus).

As used herein "histones" are proteins involved in which package and order the genomic DNA into structural units called nucleosomes, which in turn make up the chromatin, i.e. the combination of DNA and proteins that makes up chromosomes. Histone modifications are post-translational modifications of particular amino acid residues in the N-terminal region of histones (histon tails). Some histone modifications, such as acetylation and particular types of phosphorylation and ubiqitination are associated with active gene transcription and relaxed chromatin, whereas e.g. biotinylation and sumoylation are associated with gene repression and inactive, i.e. condensed chromatin. Also the types of histones that are incorporated into the chromatin influences chromatin compaction. Environmental stresses can modulate this so-called histone code to influence gene expression (Chinnusamy et al., 2009, Curr Opin Plant Biol 12: p1-7, Urano et al., 2010, Curr Opin. Plant Biol. 13, p132-138).

As used herein "DNA methylation", refers to the addition of a methyl group to the 5 position of the cytosine (C) pyrimidine ring or the number 6 nitrogen of the adenine (A) purine ring. DNA methylation is generally associated with gene repression and inactive chromatin. Methylation of DNA mostly takes place on cytosines, and in plants occurs both asymmetriccally (mCpHpH) and symmetriccally (mCpG and mCpHpG). DNA methylation is established by de novo methyltransferases (e.g. DRM1 and DMR2), which in plants are guided to their targets by small RNAs. Symmetric methylation patterns are maintained after DNA replication by maintenance methyltransferases, which methylate the new DNA strand based on the pattern found on the parent strand. Maintenaince methylation (i.e. after cell division) is mediated by other methylase enzymes such as the maintenance methylases MET1 and CMT3, although it has recently become apparent that both types of enzymes may also perform the other type of methylation. Demethylation is a process that is less well understood. Methylation can be lost either passively, when the maintenance methylation that usually follows DNA replication is inhibited, or by a more active process when 5-methylcytosine is enzymatically removed. In this process, DNA glycosylases, which are normally associated with DNA repair, recognize and remove 5-methylcytosine from DNA, leading to its replacement with cytosines, a process known as DNA base-excision-repair. However, there are also indications of the presence of enzymes that actively remove 5-methylcytosine from DNA (Chinnusamy et al., 2009, Curr Opin Plant Biol 12: p1-7; Gehring et al., 2009, Trends in Genetics Vol. 25, p82-90). Environmental stresses also have an effect of DNA methylation, e.g. cold stress was found to induce DNA hypomethylation, whereas osmotic stress was found to induce hypermethylation (Chinnusamy et al., 2009, supra).

DNA methylation can be assessed using various techniques know in the art, such as, but not exclusively, via Methylation-sensitive restriction endonucleases like Methylation sensitive Amplified Fragments Length Polymorphism (MSAP) as described in e.g. Matthes et al. (2001, Theor Appl Genet 102: p971-979), Bisulphite treatment of DNA followed by sequencing, Methylated DNA immunopirecipitation, shotgun bisulphate sequencing, as all described in e.g. Chinnusamy et al. (2009, Curr Opin Plant Biol 12: p1-7), Methylation specific quantum dot fluorescence resonance energy transfer (MS-qFRET) as e.g. described in Bailey et al. (2010, Methods. 2010 Apr. 1), cytosine extension assay as e.g. described in Hauben et al., 2009 (supra) and via methyl-CpG-binding proteins combined with fluorescence/Förster resonance energy transfer (FRET) or fluorescently labeled antigen binding fragments of specific antibodies as e.g. described in Kimura et al. (2010, Curr Opin Cell Biol. March 4.).

As used herein, H refers to any of the nucleotides A, T or C, while Y refers to any of the nucleotides C or T.

As used herein "a population of genetically uniform plants", is a population of plants, wherein the individual plants are true breeding, i.e. show little or no variation at the genome nucleotide sequence level, at least for the genetic factors which are underlying the quantitative trait, particularly genetic factors underlying high energy use efficiency and low cellular respiration rate. Genetically uniform plants may be inbred plants but may also be a population of genetically identical plants such as doubled haploid plants. Doubled haploid plants are plants obtained by spontaneous or induced doubling of the haploid genome in haploid plant cell lines (which may be produced from gametes or precursor cells thereof such as microspores). Through the chromosome doubling, complete homozygous plants can be produced in one generation and all progeny plants of a selfed doubled haploid plant are substantially genetically identical (safe the rare mutations, deletions or genome rearrangements). Other genetically uniform plants are obtained by vegetal reproduction or multiplication such as e.g. in potato, sugarcane, trees including poplars or eucalyptus trees. Genetically uniform plants may also be referred to as "isogenic".

As used herein, "energy use efficiency (EUE)" is the quotient of the "energy content" and "cellular respiration". High energy use efficiency can be achieved in plants when the energy content of the cells of the plant remains about equal to that of control plants, but when such energy content is achieved by a lower cellular respiration. Plant with a high EUE are also said to have a high fitness or vigor. A plant can be called fit or vigorous when this line grows vitally, healthy, is tolerant to various biotic and abiotic stresses and most importantly has a high yield.

As used herein, increased yield refers to an increase of yield at least 1%, at least 2%, at least 3%, at least 4%, at least 5% or more when compared to a control plant or to the average of a population.

As used herein, "heterosis effect" or "hybrid vigour" is used to refer to the superiority of heterozygous genotypes with respect to one or more characters, particularly with regard to a character of interest such as yield, in comparison with the corresponding homozygotes.

Whenever reference to a "plant" or "plants" according to the invention is made, it is understood that also plant parts (cells, tissues or organs, seed pods, seeds, severed parts such as roots, leaves, flowers, pollen, etc.), progeny of the plants which retain the distinguishing characteristics of the parents, such as seed obtained by selfing or crossing, e.g. hybrid seed (obtained by crossing two inbred parental lines), hybrid plants and plant parts derived there from are encompassed herein, unless otherwise indicated.

A "variety" is used herein in conformity with the UPOV convention and refers to a plant grouping within a single botanical taxon of the lowest known rank, which grouping can be defined by the expression of the characteristics resulting from a given genotype or combination of genotypes, can be distinguished from any other plant grouping by the expression of at least one of the said characteristics and is considered as a unit with regard to its suitability for being propagated unchanged (stable).

The term "comprising" is to be interpreted as specifying the presence of the stated parts, steps or components, but does not exclude the presence of one or more additional parts, steps or components. A plant comprising a certain trait may thus comprise additional traits.

It is understood that when referring to a word in the singular (e.g. plant or root), the plural is also included herein (e.g. a plurality of plants, a plurality of roots). Thus, reference to an element by the indefinite article "a" or "an" does not exclude the possibility that more than one of the element is present, unless the context clearly requires that there be one and only one of the elements. The indefinite article "a" or "an" thus usually means "at least one".

DETAILED DESCRIPTION

The invention is based on the observation that isogenic plant lines that have been selected for either high or low vigor based on their energy use efficiency (EUE) over multiple generations of backcrossing (Hauben et al, 2009) display distinct epigenetic profiles during development. Low vigor lines LV80, LV82, high vigor lines HV76, HV77 and HV76-derived line "crashed", which resembles the high vigor lines in the cotyledon stage but low vigor lines later in development, as well as their parental line "Simon", were evaluated for changes in their genomic DNA methylation pattern (cytosine methylation) between the cotyledon and the 3th leaf stage. It was found that low EUE/vigor plants are characterized by no changes in methylated cytosines, whereas high EUE/vigor plants are characterized by changes in cytosine methylation, i.e. demethylation and de novomethylation) and no changes in unmethylated cytosines during growth. The most evident epigenetic feature characteristic for high vigor plants appeared the loss of cytosine methylation in a mCCG context.

A method is described for selecting a population of plants, such as *Brassica* oilseed rape, tomato plants or rice plants, or seeds thereof with a high energy use efficiency comprising the following steps:

a. providing an population consisting of a plurality of individual plants which are genetically uniform;
b. isolating a tissue sample or explant from individual plants of said population in a manner which allows further cultivation of said sampled individual plants;
c. optionally, culturing said tissue samples or explants under conditions which activate the metabolism in said plants;
d. determining the cellular respiration rate of said individual plants by analyzing said samples of said plants;
e. selecting a number of plants wherein said sample exhibits a cellular expiration which is lower, preferably is significantly lower, than the average cellular respiration of samples from said population;
f. growing the selected plants and propagating from each of the selected plants a line of cloned progeny plants;
g. determining the energy use efficiency for each line of cloned progeny plants;

h. selecting a line of clone plants wherein said energy use efficiency is higher, than the average of the energy use efficiency of all lines of cloned progeny plants, preferably select the line of clone progeny plants with the highest energy use efficiency.

i. growing a population of individual plants from said selected line of clone progeny plants; and j. reiterating at least once steps b to i on said subsequent population.

The energy use efficiency can be determined by determining the cellular respiration and determining the NAD(P)H content in the isolated sample and dividing the NAD(P)H content by the respiration to determine the energy use efficiency. The energy use efficiency can also be determined by measuring the ascorbate or ascorbic acid content of the plant or by measuring the respiratory chain complex I activity in said sample.

The provided methods include identifying plants with high energy use efficiency by determining the cellular respiration in said sample and at least one of the following parameters: ascorbate content; NAD(P)H content; respiratory chain complex I activity; or photorespiration; and selecting those plants with lower cellular respiration and a higher ascorbate content, or a higher respiratory chain complex I activity or lower photorespiration than the control plants (i.e. plants of the original population which have not been subjected to the repeated selection scheme for low cellular respiration). Typically cellular respiration rate may be between 85 and 95% of the cellular respiration rate of a control plant and NAD(P)H content may be between 95 to 105% of of the NAD(P)H content of a control plant. Respiratory chain complex I activity may typically be between 120 to 140% of the respiratory chain complex I activity of a control plant and ascorbate content may be between 150 to 220% of the ascorbate content of a control plant. Photorespiration is preferably between 80 to 92% of the photorespiration of a control plant.

As used herein, "energy use efficiency" is the quotient of the "energy content" and "cellular respiration". High energy use efficiency can be achieved in plants when the energy content of the cells of the plant remains about equal to that of control plants, but when such energy content is achieved by a lower cellular respiration.

"Cellular respiration" refers to the use of oxygen as an electron acceptor and can conveniently be quantified by measuring the electron transport through the mitochondrial respiratory chain e.g. by measuring the capacity of the tissue sample to reduce 2,3,5 triphenyltetrazolium chloride (TTC). Although it is believed that for the purpose of the assays defined here, TTC is the most suited substrate, other indicator molecules, such as MTT (3-(4,5-dimethylthiazol-2-yl)-2,5 diphenyl-2H-tetrazolium), can be used to measure the electron flow in the mitochondrial electron transport chain (see Musser and Oseroff, 1994 *Photochemistry and Photobiology* 59, pp 621-626). TTC reduction occurs at the end of the mitochondrial respiratory chain at complex IV. Therefore, TTC reduction reflects the total electron flow through the mitochondrial respiratory chain, including the alternative oxidative respiratory pathway. The electrons enter the mitochondrial electron transport chain through complex I, complex II, and the internal and external alternative NAD(P)H dehydrogenases. A suitable TTC reduction assay has been described by De Block and De Brouwer, 2002 (*Plant Physiol. Biochem.* 40, 845-852).

The "energy content" of cells of a plant refers to the amount of molecules usually employed to store energy such as ATP, NADH and NADPH. The energy content of a sample can conveniently be determined by measuring the NAD(P)H content of the sample. A suitable assay has been described by Nakamura et al. 2003. (Quantification of intracellular NAD(P)H can monitor an imbalance of DNA single strand break repair in base excision repair deficient cells in real time. *Nucl. Acids Res.* 31, 17 e104).

In a first embodiment, the invention therefore relates to a method which allows the selection of one ore more plants (e.g. a subpopulation) with a high energy use efficiency ("EUE") and thus a high yield, particularly seed yield potential, from an initial population of plants from the same species or variety, e.g. genetically uniform plants. High energy use efficiency is a quantitative trait for which variability (along a normal distribution curve) exists within a population of (genetically uniform) plants. The method comprises the following steps:

a. providing a population consisting of a plurality of individual plants;

b. obtaining a genomic DNA sample from individual plants of said collection/population at least a first and a second developmental stage in a manner which allows further cultivation of said sampled individual plants;

c. determining of each of said individual plants the methylation profile of said genomic DNA obtained at said at least two stages;

d. determining the epigenetic features of each of said individual plants by evaluating the changes in DNA methylation profile between said first and said second stage;

e. identifying and selecting at least one plant which has a high relative occurrence of epigenetic features characteristic for high energy use efficiency when compared to other plants of said population, wherein said epigenetic characteristics are selected from:

i. changes (gain and/or loss) of methylated cytosines (mC); and/or ii. no changes in unmethylated cytosines (C)

As used herein, "a high relative occurrence when compared to other plants of the population", refers to the occurrence of an epigenetic feature characteristic for high EUE that is higher than the average occurrence of that epigenetic feature in that population. Preferably, the plant or plants are selected that have the highest occurrence of the most of those epigenetic features. "A high relative occurrence" with respect to other plants of the population or the average of the population refers to an occurrence that is at least 1%, at least 5%, at least 10%, at least 15%, at least 20% lower, at least 30% lower, at least 40% lower, at least 50% higher than the occurrence in another plant of the population or than the average occurrence of a particular epigenetic feature of the population.

As used herein, epigenetic features that are characteristic for high EUE, is intended to mean those changes or no changes in DNA methylation that have been most frequently observed between the developmental stages in plants with a high EUE (i.e. higher than the average of the population) when compared to plants with a lower EUE (i.e. lower than the average of the population), comprising gain and/or loss of methylated cytosines (mC) and/or no changes in unmethylated cytosines (C). Preferably, the changes in mC occur within a mCG, mCHG and/or mCHH context. The no changes in C preferably occur within a CG, CHG and/or CHH context.

More specifically, those features comprise no changes in CTT, mCTT-gain, no changes in CCG, no changes in CG, mCTC-gain, mCG-gain, mCTG-loss, mCTT-loss and mCCG-loss.

Thus, in a further embodiment, the at least one plant that is selected has a relative high occurrence of at least five epigenetic features that are characteristic for high energy use efficiency when compared to other plants of that population, wherein those epigenetic features are selected from the group consisting of: no changes in CTT, mCTT-gain, no changes in CCG, no changes in CG, mCTC-gain, mCG-gain, mCTG-loss, mCTT-loss and mCCG-loss.

In a further embodiment, the at least five epigenetic features comprise mCTC-gain, mCG-gain, mCTG-loss, mCTT-loss and mCCG-loss.

In another embodiment, the method of the invention relates to selecting the at least one plant which has a high relative occurrence of at least eight of the epigenetic features no changes in CTT, mCTT-gain, no changes in CCG, no changes in CG, mCTC-gain, mCG-gain, mCTG-loss, mCTT-loss and mCCG-loss, when compared to other plants of said population.

In yet another embodiment, the at least one plant that is selected has a high relative occurrence of mCCG-loss when compared to other plants of said population, preferably the highest.

It was furthermore found that when the clustering analysis was restricted to epigenetic markers that were polymorphic at the first developmental stage (i.e. markers that were monomorphic at the first developmental stage were excluded), high EUE plants were characterized by the following epigenetic features: mCTG-loss, mCG-gain, mCTA-loss, no change in CCG-mCCG, mCTC-gain, mCTT-gain, no change in CTC-mCTC or mCTG-gain.

Thus, the invention also provides a method to produce a plant with a high energy use efficiency from a collection of plants from the same species or variety comprising the steps of:
  a) providing a population consisting of a plurality of individual plants;
  b) obtaining a genomic DNA sample from individual plants of said collection/population at least a first and a second developmental stage in a manner which allows further cultivation of said sampled individual plants;
  c) determining of each of said individual plants the methylation profile of said genomic DNA obtained at said at least two stages;
  d) determining the epigenetic features of each of said individual plants by evaluating the changes in DNA methylation profile between said first and said second stage;
  e) identifying and selecting at least one plant which has a high relative occurrence of at least four epigenetic features characteristic for high energy use efficiency when compared to other plants of said population, wherein said epigenetic features are selected from: mCTG-loss, mCG-gain, mCTA-loss, no change in CCG-mCCG, mCTC-gain, mCTT-gain, no change in CTC-mCTC or mCTG-gain,
  wherein said epigenetic features have been determined based on markers that are polymorphic at said first stage.

In an even further embodiment, the selected at least one plant has a high relative occurrence of at least five or at least six of said selected epigenetic features that are characteristic for high energy use efficiency when compared to other plants of said population when the epigenetic features have been determined based on markers that are polymorphic at said first stage.

Further provided is a method to produce a plant with a high energy use efficiency from a collection of plants from the same species or variety comprising the steps of:
  a) providing a population consisting of a plurality of individual plants;
  b) obtaining a genomic DNA sample from individual plants of said collection/population at least a first and a second developmental stage in a manner which allows further cultivation of said sampled individual plants;
  c) determining of each of said individual plants the methylation profile of said genomic DNA obtained at said at least two stages;
  d) determining the epigenetic features of each of said individual plants by evaluating the changes in DNA methylation profile between said first and said second stage;
  e) identifying and selecting at least one plant which has a high relative occurrence of at least four epigenetic features characteristic for high energy use efficiency when compared to other plants of said population, wherein said epigenetic features are selected from: mCTG-loss, mCG-gain, mCTA-loss, no change in CCG-mCCG, mCTC-gain or mCTT-gain,
  wherein said epigenetic features have been determined based on markers that are polymorphic at said first stage.

Alternatively, high vigor plants can also be obtained by selecting for a low relative occurrence of epigenetic features that are characteristic for low energy use efficiency. As used herein, epigenetic features that are characteristic for low EUE, is intended to mean those changes or no changes in DNA methylation that have been most frequently observed between the developmental stages in plants with a low EUE (i.e. lower than the average of the population) when compared to plants with a higher EUE (i.e. lower than the average of the population), such as no changes in methylated cytosines, preferably of mCTH and a gain in methylation on mCHH. More specifically those epigenetic features include mCTA-loss, no changes in CTC, mCCG-gain, no change in mCG, mCTA-gain, no change in mCTG, no change in mCTT, no change in mCTC, no change in CTG, no change in mCTA.

As used herein, "a low relative occurrence when compared to other plants of the population", refers to the occurrence of an epigenetic feature characteristic for low EUE that is lower than the average occurrence of that epigenetic feature in that population. Preferably, to select for high EUE, the plant or plants are selected that have the lowest occurrence of the most of those epigenetic features.

"A low relative occurrence" with respect to other plants of the population or the average of the population refers to an occurrence that is at least 1%, at least 5%, at least 10%, at least 15%, at least 20% lower, at least 30% lower, at least 40% lower, at least 50% lower than the occurrence in another plant of the population or than the average occurrence of a particular epigenetic feature of the population.

Thus, in another embodiment the invention provides a method to produce a plant with high energy use efficiency from a collection of plants from the same species or variety comprising the steps of:
  a) providing a population consisting of a plurality of individual plants;
  b) obtaining a genomic DNA sample from individual plants of said collection/population at least a first and a second developmental stage in a manner which allows further cultivation of said sampled individual plants;

c) determining of each of said individual plants the methylation profile of said genomic DNA obtained at said at least two stages;
d) determining the epigenetic features of each of said individual plants by evaluating the changes in DNA methylation profile between said first and said second stage;
e) identifying and selecting at least one plant which has a low relative occurrence of epigenetic features characteristic for low energy use efficiency when compared to other plants of said population, wherein said epigenetic features characteristic for a low energy use efficiency are selected from:
   i) no changes in methylated cytosines, preferably of mCTH
   ii) gain in methylation on mCHH More specifically, those features characteristic for low EUE comprise: mCTA-loss, CTC-unchanged, mCCG-gain, mCG-unchanged, mCTA-gain, mCTG-unchanged, mCTT-unchanged, mCTC-unchanged, CTG-unchanged, mCTA-unchanged.

Thus, in a further embodiment, said selected at least one plant has a low relative occurrence of at least five epigenetic features that are characteristic for low energy use efficiency when compared to other plants of said population, wherein said epigenetic features that are characteristic for low energy use efficiency are selected from the group consisting of: mCTA-loss, CTC-unchanged, mCCG-gain, mCG-unchanged, mCTA-gain, mCTG-unchanged, mCTT-unchanged, mCTC-unchanged, CTG-unchanged, mCTA-unchanged.

In an even further embodiment, the selected at least one plant has a low relative occurrence of at least six or at least seven, or at least eight, or at least nine of said selected epigenetic features that are characteristic for low energy use efficiency when compared to other plants of said population.

In another embodiment, the selected at least one plant with high EUE has a low relative occurrence of the epigenetic features mCCG-gain, mCTA-gain or mCG-unchanged, or a combination of two or three of those features, when compared to other plants of said population.

When selecting only markers that are polymorphic at the first developmental stage, low EUE lines appeared to be characterized by a high relative occurrence of the following epigenetic features: no change in CTT-mCTT, mCTC-loss, mCCG-loss, mCG-loss, mCTA-gain, no change in CTG-mCTG, mCCG-gain, no change in CG-mCG, mCTT-loss, no change in CTA-mCTA, particularly mCTA-gain, no change in CTG-mCTG, mCCG-gain.

Thus, in another embodiment, the invention provides a method to produce a high EUE plant from a collection of plants from the same species or variety comprising the steps of:
   a) providing a population consisting of a plurality of individual plants;
   b) obtaining a genomic DNA sample from individual plants of said collection/population at least a first and a second developmental stage in a manner which allows further cultivation of said sampled individual plants;
   c) determining of each of said individual plants the methylation profile of said genomic DNA obtained at said at least two stages;
   d) determining the epigenetic features of each of said individual plants by evaluating the changes in DNA methylation profile between said first and said second stage;
   e) identifying and selecting at least one plant which has a low relative occurrence of at least six epigenetic features that are characteristic for low energy use efficiency when compared to other plants of said population, wherein said epigenetic features that are characteristic for low energy use efficiency are selected from the group consisting of: no change in CTT-mCTT, mCTC-loss, mCCG-loss, mCG-loss, mCTA-gain, no change in CTG-mCTG, mCCG-gain, no change in CG-mCG, mCTT-loss or no change in CTA-mCTA wherein said epigenetic features have been determined based on markers that are polymorphic at said first stage.

In an even further embodiment, the selected at least one plant has a low relative occurrence of at least seven of said selected epigenetic features that are characteristic for low energy use efficiency when compared to other plants of said population when the epigenetic features have been determined based on markers that are polymorphic at the first stage.

In another embodiment, the selected at least one plant with high EUE has a low relative occurrence of the epigenetic features mCTA-gain, no change in CTG-mCTG, mCCG-gain, or a combination of two or three of those features, when compared to other plants of said population when the epigenetic features have been determined based on markers that are polymorphic at the first stage.

It has been observed that the selected subpopulation with high EUE were more tolerant to adverse abiotic conditions than the unselected control plants. Accordingly, the invention also provides a method for producing a population of plants or seeds with increased tolerance to adverse abiotic conditions by selection plants or populations of plants according to the methods described herein. As used herein "adverse abiotic conditions" include drought, water deficiency, hypoxic or anoxic conditions, flooding, high or low suboptimal temperatures, high salinity, low nutrient level, high ozone concentrations, high or low light concentrations and the like.

As the yield improvement obtained by selecting subpopulation of plants or plants with high energy use efficiency can be transmitted to subsequent generations in sexual crosses (behaving as a dominant or co-dominant factor) and as that yield improvement in hybrid plants moreover is additional to the normal yield increase due to hybrid vigor, a further embodiment of the invention provides a method for producing a hybrid plant or hybrid seed with high yield or tolerance to adverse abiotic conditions comprising:
   a. selecting a population of plants with high energy use efficiency according to the methods herein described for at least one parent inbred plant;
   b. crossing plants of that population with another inbred plant;
   c. isolating hybrid seed of the cross; and
   d. optionally, grow hybrid plants from the seed.

The selection scheme may further be applied to both parent lines and if hybrid production involves male sterility necessitating the use of a maintainer line for maintaining the female parent, the selection schemes described herein may also be beneficially used on the maintainer lines.

The selection scheme has been successfully applied on rice plant populations, *Brassica napus* plant populations and *Lycopersicon esculentum* plant populations. Nevertheless, the methods and means described herein are believed to be suitable for all plant cells and plants, gymnosperms and angiosperms, both dicotyledonous and monocotyledonous plant cells and plants including but not limited to *Arabidopsis*, alfalfa, barley, bean, corn or maize, cotton, flax, oat, pea, rape, rice, rye, safflower, sorghum, soybean, sunflower, tobacco and other *Nicotiana* species, including *Nicotiana benthamiana*, wheat, asparagus, beet, broccoli, cabbage, carrot, cauliflower, celery, cucumber, eggplant, lettuce, onion, oilseed rape, pepper, potato, pumpkin, radish, spinach, squash, tomato, zucchini, almond, apple, apricot, banana, blackberry, blueberry, cacao, cherry, coconut, cranberry, date, grape, grapefruit, guava, kiwi, lemon, lime, mango, melon, nectarine, orange, *papaya*, passion fruit, peach, peanut, pear, pineapple, pistachio, plum, raspberry, strawberry, tangerine, walnut and watermelon *Brassica* vegetables, sugarcane, vegetables (including chicory, lettuce, tomato), Lemnaceae (including species from the genera *Lemna, Wolffiella, Spirodela, Landoltia, Wolffia*) and sugarbeet.

The methods described herein may also be used for the identification of physiological conditions or compounds that affect the performance (vigor, EUE, yield, abiotic stress tolerance etc) of a plant or collection of plants, or to discriminate mutant plants, cells or cell lines from wild-types.

Thus, in yet another embodiment the invention provides for a method for obtaining a biological or chemical compound which is capable of generating a plant with high energy use efficiency comprising a) providing a population of plants of the same plant species, b) subjecting said population of plants with a biological or chemical compound, c) obtaining a genomic DNA sample from individual plants of said collection/population at least a first and a second developmental stage in a manner which allows further cultivation of said sampled individual plants; d) determining of each of said individual plants the methylation profile of said genomic DNA obtained at said at least two stages; e) determining the epigenetic features of each of said individual plants by evaluating the changes in DNA methylation profile between said first and said second stage, wherein the high relative presence of epigenetic features in the methylation profile that are characteristic for a high EUE, i.e. selected from i) gain and/or loss of methylated cytosines, preferably of mCG, mCHG and/or mCHH; and/or ii) no changes in C, preferably of CG, CHG and/or CHH is indicative for a biological compound capable of generating a plant with a high energy use efficiency. Alternatively, the relative low presence of epigenetic features that are characteristic for low EUE, as described above, is also indicative for a biological compound capable of generating a plant with a high energy use efficiency.

In step (b) any biological or chemical compound may be contacted with the plants or plant parts. It is also envisaged that a plurality of different compounds can be contacted in parallel with plants or plant parts. Preferably each test compound is brought into physical contact with one or more individual plants. Contact can also be attained by various means, such as spraying, spotting, brushing, applying solutions or solids to the soil, to the gaseous phase around the plants or plant parts, dipping, etc. The test compounds may be solid, liquid, semi-solid or gaseous. The test compounds can be artificially synthesized compounds or natural compounds, such as proteins, protein fragments, volatile organic compounds, plant or animal or microorganism extracts, metabolites, sugars, fats or oils, microorganisms such as viruses, bacteria, fungi, etc. In a preferred embodiment the biological compound comprises or consists of one or more microorganisms, or one or more plant extracts or volatiles (e.g. plant headspace compositions). The microorganisms are preferably selected from the group consisting of: bacteria, fungi, mycorrhizae, nematodes and/or viruses. It is especially preferred and evident that the microorganisms are non-pathogenic to plants, or at least to the plant species used in the method. Especially preferred are bacteria which are non-pathogenic root colonizing bacteria and/or fungi, such as Mycorrhizae. Mixtures of two, tree or more compounds may also be applied to start with, and a mixture which shows an effect on priming can then be separated into components which are retested in the method. Using mixtures, also synergistically acting compounds can be identified, i.e. compounds which provide a stronger priming effect together than the sum of their individual priming effect. Preferably compositions are liquid or solid (e.g. powders) and can be applied to the soil, seeds or seedlings or to the aerial parts of the plant.

In a particular embodiment in the method for obtaining a biological or chemical compound, the epigenetic features are selected from the group consisting of: no change in CTT-, mCTT-gain, no change in CCG, no change in CG, mCTC-gain, mCG-gain, mCTG-loss, mCTT-loss and mCCG-loss.

In yet another embodiment the invention provides a differential DNA methylation profile, characterized in that at least five epigenetic features characteristic for high energy use efficiency are detected in the genomic DNA of a plant between a first and a second developmental stage said plant, wherein said epigenetic features are selected from: i) a gain and/or loss of methylated cytosines, preferably of mCG, mCHG and/or mCHH; and/or ii) no changes in unmethylated cytosines, preferably of CG, CHG and/or CHH. More specifically, said at least five epigenetic features are selected from no change in CTT-, mCTT-gain, no change in CCG, no change in CG, mCTC-gain, mCG-gain, mCTG-loss, mCTT-loss or mCCG-loss.

When selecting only first stage polymorphic markers, said differential DNA methylation profile is characterized in that at least four epigenetic features characteristic for high energy use efficiency are detected in the genomic DNA of a plant between a first and a second developmental stage said plant, wherein said epigenetic features are selected from mCTG-loss, mCG-gain, mCTA-loss, no change in CCG-mCCG, mCTC-gain, mCTT-gain, no change in CTC-mCTC or mCTG-gain.

Alternatively, the differential DNA methylation profile characteristic for high EUE can also be characterized by the low relative occurrence of epigenic features that are characteristic for a low EUE as described above.

In yet another embodiment the invention provides for a use of the differential DNA methylation profile to carry out the methods for the production of a plant with a high energy efficiency described herein before.

In yet another embodiment the differential DNA methylation profile is used in the method for obtaining a biological or chemical compound which is capable of generating a plant with a high energy use efficiency.

The methods described herein may also be used to classify individual plants of a particular plant variety or plant line according to their performance.

The invention also related to the production of plants with increased vigor/EUE by promoting the occurrence of epigenetic features that are characteristic for high EUE, by e.g. treatment with compounds that influence particular DNA methylation states (e.g. 5-aza-cytidine), or by modulating the expression of RNAs or proteins and the like that are directly or indirectly involved in DNA methylation, such as DNA methylases or demethylases, small RNAs, histone modifying enzymes.

In the description and examples, reference is made to the following sequences:

Sequences
SEQ ID NO. 1: AluI adaptor A
SEQ ID NO. 2: AluI adapter B
SEQ ID NO. 3: EcoR1 adapter A
SEQ ID NO. 4: EcoR1 adapter B
SEQ ID NO. 5: HaeIII adapter A
SEQ ID NO. 6: HaeIII adapter B
SEQ ID NO. 7: MH adapter A
SEQ ID NO. 8: MH adapter B
SEQ ID NO. 9: Mse1 adapter A
SEQ ID NO. 10: Mse1 adapter B
SEQ ID NO. 11: primer A1
SEQ ID NO. 12: primer A2
SEQ ID NO. 13: primer A3
SEQ ID NO. 14: primer A4
SEQ ID NO. 15: primer E1
SEQ ID NO. 16: primer HA0
SEQ ID NO. 17: primer MH1
SEQ ID NO. 18: primer MH2
SEQ ID NO. 19: primer MH3
SEQ ID NO. 20: primer MH4
SEQ ID NO. 21: primer M2
SEQ ID NO. 22: primer A37
SEQ ID NO. 23: primer A40
SEQ ID NO. 24: primer A41
SEQ ID NO. 25: primer A47
SEQ ID NO. 26: primer A50
SEQ ID NO. 27: primer A51
SEQ ID NO. 28: primer A67
SEQ ID NO. 29: primer A70
SEQ ID NO. 30: primer A71
SEQ ID NO. 31: primer A88
SEQ ID NO. 32: primer A89
SEQ ID NO. 33: primer A94
SEQ ID NO. 34: primer E33
SEQ ID NO. 35: primer HA67
SEQ ID NO. 36: primer MH18
SEQ ID NO. 37: primer MH21
SEQ ID NO. 38: primer MH34
SEQ ID NO. 39: primer MH76
SEQ ID NO. 40: primer MH84
SEQ ID NO. 41: primer M47
SEQ ID NO. 42: primer M50
SEQ ID NO. 43: primer M57

EXAMPLES

The following non-limiting Examples describe methods and means according to the invention. Unless stated otherwise in the Examples, all techniques are carried out according to protocols standard in the art.

Example 1—Methodology

Artificial selection for respiration and EUE, physiological and biochemical assays, field trial and statistics were performed as described in Hauben et al. (2009) Proc Natl Acad Sci USA November 24; 106(47):20109-14 and in the examples 1 and 2 of the priority application EP09075284 (filed on 1 Jul. 2009), both of which references are incorporated herein by reference.

Example 1A. Methodology

Artificial selection for respiration and EUE. Seedlings were grown in vitro for two weeks on agar medium half concentrated Murashige and Skoog medium supplemented with 2% sucrose. The shoot tips of the seedlings were put on the above medium for rooting, while five hypocotyl explants per seedling were cultured for five days on callus inducing medium (Murashige and Skoog medium supplemented with 3% sucrose and 1 mg/L 2,4-D, 0.25 mg/L NAA and 1 mg/L BAP). Cellular respiration of the hypocotyl explants was measured. The rooted shoot tips of about five seedlings with the highest respectively lowest respiration were transferred to the greenhouse for seed production by selfing. Both respiration and NAD(P)H content of about 35-40 seedlings of the obtained progenies were measured. Lines with the lowest, respectively, highest respiration and highest, respectively, lowest energy use efficiency were retained. The next rounds of selections were done in one direction for lower or higher respiration with lines having the lowest, respectively, highest respiration (FIG. 1). Three to five rounds of selection are sufficient to generate lines with distinct respiration and EUE. The selection for respiration and EUE in the hybrid seed production is represented in FIG. 9.

Physiological and biochemical assays. Cellular respiration of hypocotyl explants was quantified by measuring the reduction of 2,3,5-triphenyltetrazoliumchloride (TTC) as described (De Block and De Brouwer, supra). Total NAD (P)H content was quantified as described (Nakamura et al. supra). Energy use efficiency is expressed as the ratio of the % normalized values versus the control of NAD(P)H content to amount of reduced TTC. Ascorbate content was quantified using the reflectometric ascorbic acid test from Merck (Darmstadt, Germany). Complex I activity was quantified using the MitoProfile Dipstick Assay kit for complex I activity of MitoSciences (Eugene, Oreg., USA). The intensity of the photorespiration was measured in vitro by floating cotyledons or leaf pieces on ammonium free medium containing 3-5 mg/L glufosinate. Incubation was done for 24 hours in continuous light (about 70 µmol $m^{-2}$ $sec^{-1}$). The ammonium production was quantified as described (De Block et al., 1995. The selection mechanism of phosphinothricin is influenced by the metabolic status of the tissue. *Planta* 197, 619-626). Photorespiration was expressed as percent produced ammonium versus control.

Field trials. Field trials were performed on five locations with different soil qualities (from sandy to loamy soil). Each location contained six plots per line. Each plot was 10 $m^2$ in size, with different arrangement of the plots for each location. Yield was expressed as kg seed/plot.

Statistics. Data were statistically analysed by one-way ANOVA with Dunnett's post test using Prism version 5.00 (GraphPad Software, San Diego, USA).

Figure 2:
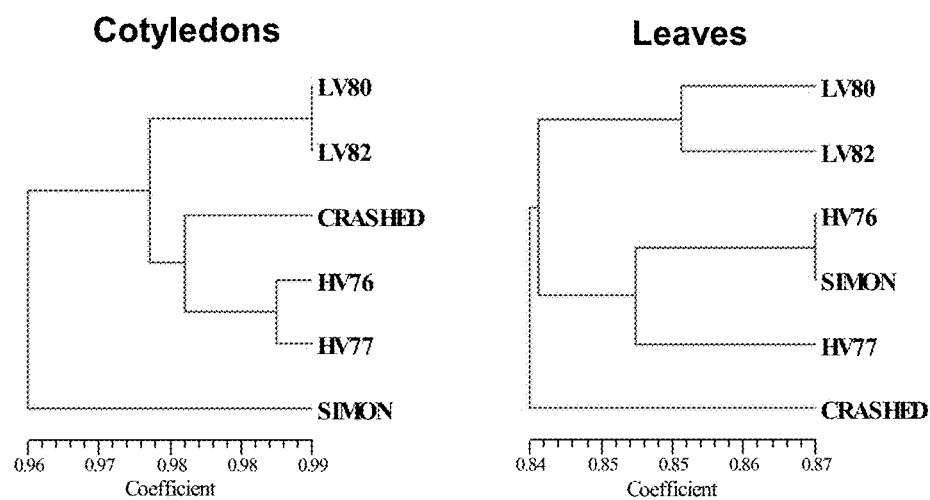
FIG. 2: Hierarchical clustering of the selected lines at the transcriptomic level (Coefficient=similarity coefficient).

Example 1B. Selection and Characterization of Selected *Brassica napus* Plants with High and Low Energy Use Efficiency Starting from an isogenic doubled haploid *B. napus* line to eliminate variation due to differences at the genetic level, seedlings with the lowest and highest cellular respiration were identified and retained (see 'Methods Summary'-FIG. 1 shows a schematic presentation of the selection scheme). In summary, starting from 200 seedlings from the doubled haploid population 'Simon' seedlings with the lowest and highest cellular respiration were identified and retained. Rooted shoot tips of five seedlings with the highest and lowest respiration, respectively, were transferred to the greenhouse for seed production by selfing. Two populations with respectively the lowest and highest EUE were identified. These two populations were the starting material for five additional rounds of selection for lines with higher and lower respiration rates, respectively. FIG. 2 shows the respiration of six lines that were generated: four lines with lower (LR76, LR76-crashed, LR77, LR79) and three lines with a higher respiration (HR80, HR82, HR83) versus the control from which the selection has been started. The 'LR76-crashed' line is derived from a further selection for lower respiration starting from line LR76. As will be shown below, the respiration of line LR76-crashed dropped below a critical threshold, resulting in a reduced vigor. At the individual plant level, there is a high variation in the high respiring lines (e.g line HR82 with a mean of 125% versus control and a standard deviation of 74%), while this variation is minimal in the low respiring lines (e.g. line LR76 with a mean of 90% versus the control and a standard deviation of 18%). From a breeder's point of view, the high variation in the high respiring lines indicates a negative behavior, while the limited variation in the low respiring lines would be scored as positive. The high efficiency with which these lines were generated (started from only 200 seedlings per selection cycle), suggests that no mutations are involved. Extensive AFLP-analyses could not identify differences between these lines and the control, except for the very high respiring line HR83 in which some chromosome deletions and inversions were detected. These plants regularly showed abnormal development and sterility. Therefore, HR83 was not retained for further analyses, together with LR79, because of its similar respiratory rate compared to the control.

Figure 3:
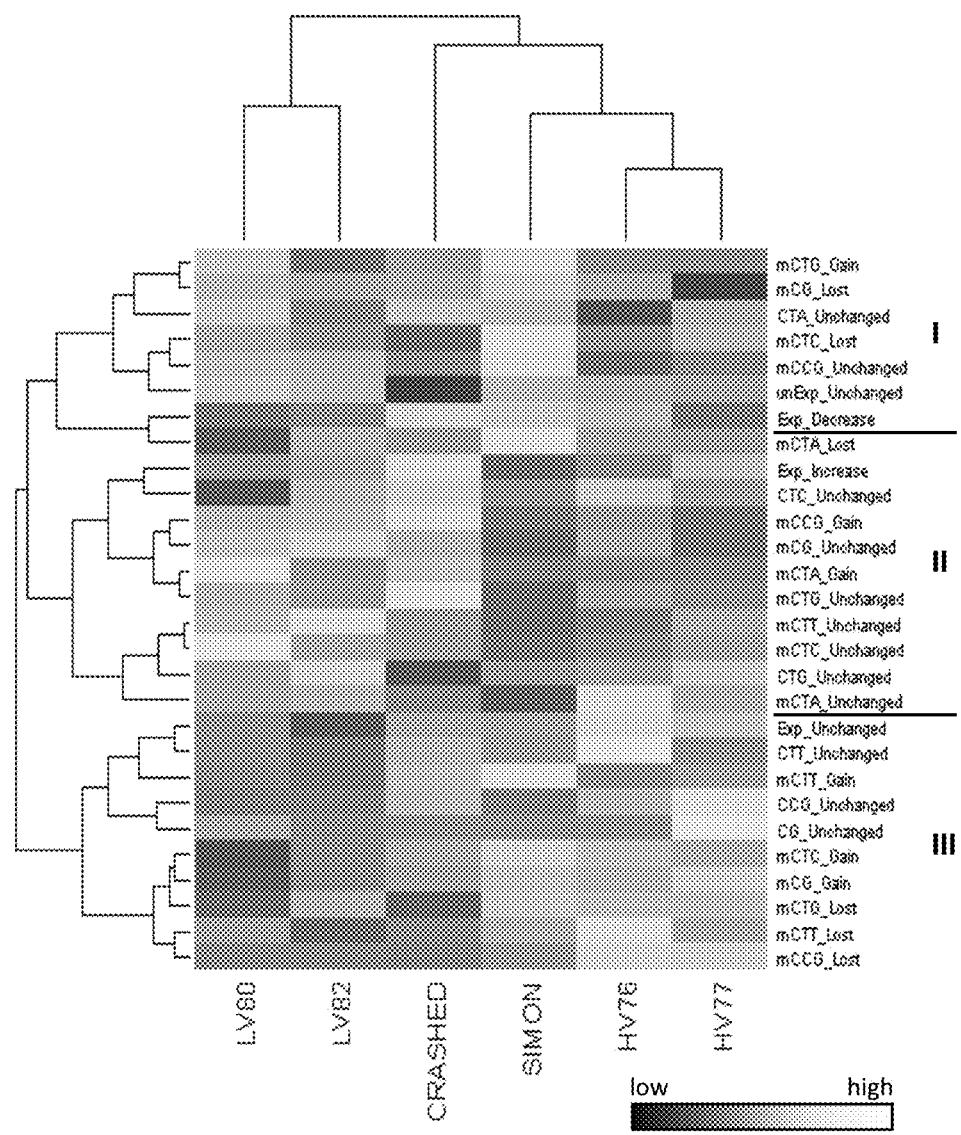
FIG. 3: Heat map depicting Spearman integrative analyses of changes and no changes in DNA methylation and expression from cotyledons to leaves in respect of the vigor/EUE of the lines.

It was expected that high cellular respiration would be linked to high energy production and vice versa. However, when the total amount of NAD(P)H, reflecting the energy content, was measured (Table 1; FIG. 3), it was noticed that lines with higher respiration had lower NAD(P)H levels. Lines with a lower respiration had a higher NAD(P)H content, except for line 'LR76-crashed'. When the ratio NAD(P)H versus respiration (energy use efficiency (EUE)) is calculated an inverse correlation is found between respiration and EUE except for the line LR76-crashed (Table 1—FIG. 3). Probably, the respiration in line LR76-crashed dropped below a critical threshold to maintain sufficient energy production.

During the selection procedure, respiration was quantified by measuring the reduction of 2,3,5-triphenyltetrazolium chloride (TTC) by hypocotyl explants. TTC reduction occurs at the end of the mitochondrial respiratory chain at complex IV (Rich, P. R., Mischis, L. A., Purton, S. & Wiskich, J. T. The sites of interaction of triphenyltetrazolium chloride with mitochondrial respiratory chains. *FEMS Microbiol. Lett.* 202, 181-187 (2001)). Therefore, TTC reduction reflects the total electron flow through the mitochondrial respiratory chain, including the alternative oxidative respiratory pathway. The electrons enter the mitochondrial electron transport chain through complex I, complex II, and the internal and external alternative NAD(P)H dehydrogenases. The activity of complex I, being the main dehydrogenase, was measured in the 3rd leaf of control and selected lines (Table 1). An inverse correlation between respiration and complex I activity was found. Recently, it was found that L-galactono-1,4-lactone dehydrogenase, the last enzyme of the plant ascorbate biosynthesis pathway, is associated with an 800-kDa subcomplex of complex I and has an important function in the accumulation of complex I as *Arabidopsis* null-mutants for L-galactone-1,4-lactone dehydrogenase fail to accumulate complex I (Pineau et al. L-galactono-1,4-lactone dehydrogenase is required for the accumulation of plant respiratory complex I. *J. Biol. Chem.* 283, 32500-32505 (2008); Millar et al. Control of ascorbate synthesis by respiration and its implications for stress responses. *Plant Physiol.* 133, 443-447 (2003)). This apparent interrelation between ascorbate biosynthesis and complex I accumulation prompted us to measure the ascorbate content in the leaves of the different lines (Table 1—FIG. 6). The lines with the highest respiration and the lowest complex I activity have the lowest ascorbate content. The reverse is also true, the lines with a low respiration and a high complex I activity have a high ascorbate content. In summary, these results suggest that lines with a high, respectively low respiratory rate have a reduced, respectively increased complex I content. The high respiring lines resemble the cytoplasmic male sterile II (CMSII) mutant of *Nicotiana sylvestris* that lacks NAD7 subunit of complex I (Guitierres et al. Lack of mitochondrial and nuclear-encoded subunits of complex I and alteration of the respiratory chain in *Nicotiana sylvestris* mitochondrial deletion mutants. *Proc. Natl. Acad. Sci. USA* 94, 3436-3441 (1997); Sabar et al. Complex I impairment, respiratory compensations, and photosynthetic decrease in nuclear and mitochondrial male sterile mutants of *Nicotiana sylvestris*. *Plant Physiol.* 124, 1239-1249 (2000))[5]. The CSMII mutant has no complex I activity but still have a high respiration due to the compensatory enhanced activity of complex IV (cytochrome oxidase). The high respiration is probably due to an enhanced activity of the alternative NAD(P)H dehydrogenases to meet the ATP needs of the cell. Lines with a high complex I content are more efficient in producing ATP resulting in a lower respiratory rate.

In tobacco and cucumber, it was found that decreased complex I capacity result in an increase in photorespiration (Juczczuk et al. Effect of mitochondrial genome rearrangement on respiratory activity, photosynthesis, photorespiration and energy status of MSC16 cucumber (*Cucumis sativus*) mutant. *Physiol. Plant.* 131, 527-541 (2007); Priault et al. The lack of mitochondrial complex I in a CMSII mutant of *Nicotiana sylvestris* increases photorespiration through an increased internal resistance to CO diffusion. *J. Exp. Bot.* 57, 3195-3207 (2006)). Similarly, we also found that the high respiring *Brassica* lines have a significant increased photorespiration, while the low respiring lines have a strongly reduced photorespiration (Table 1—FIG. 7). This implies that low respiration (but not a too low respiration as in the LR76-crashed line) correlates with a favorable physiological state, while high respiration correlates with a lower fitness. The specific characteristics of the physiological states indicate that these lines have a higher, respectively lower, stress tolerance and field performance. The selected lines and the control line were tested for seed yield in field trials (five locations with three to six replications of ten square meter per line) during three years. Low respiring lines with a high EUE had on average up to 8% higher seed yield versus the control, while high respiring lines with low EUE had on average a seed yield reduction of up to 10%. In fields with moderate drought stress the best high EUE line had 20% higher yield versus the control, while the seed yield of the high respiring and low EUE line dropped 20%. There is a strong positive correlation between EUE and seed yield (Pearson correlation=0.96).

The high efficiency with which the high and low respiring lines were generated starting from an isogenic line and the fact that the selected lines are indistinguishable from each other, based on our AFLP results, suggest that the distinct physiological characteristics of the lines have an epigenetic basis.

From the about eight generations of seed scaling up in the greenhouse and three years of elaborate field trials, it has become obvious that the epigenetic state of the lines is stably inherited by selfings. As described before for the epigenetic recombination component in *Arabidopsis* (Molinier et al. Transgeneration memory of stress in plants. *Nature* 442, 1046-1049 (2006)), the epigenetic respiration component of canola can be transmitted in reciprocal backcrosses with a non-selected control line. For example, in the high respiring line HR82, the selfing and the backcrosses to the original Simon line with HR82 as female and male resulted in progenies with respectively 127%, 124% and 128% respiration versus the control. The same was true for the low respiring line LR77 of which the selfing and backcrosses to Simon with LR77 as female and male resulted in progenies with respectively 89%, 91% and 92% versus the control.

Our results show that it is feasible to select for a complex trait solely based on directing the epigenetic component. The main difference with the selection in classical breeding schemes is that selection may not only be done at the population but primary at the plant level and this in a recursive way. By applying the same selection schemes on elite parental lines of canola, we generated hybrids that have up to 5% higher yields additive on the yield increase by heterosis. This shows the general utility of the selection method in canola and confirms the transgenerational stability of the epigenetic respiration component. Experiments further indicate that this type of selection is also feasible in other plant species such as rice and tomato.

Example 2—Selection and Characterization of Selected *Brassica napus* Plants with High and Low Energy Use Efficiency Selection of *B. napus* plants with high EUE/vigor (HV76, HV77) and low EUE/vigor (LV80, LV82, crashed) was performed as described in Hauben et al. (2009) Proc Natl Acad Sci USA November 24; 106(47):20109-14 and in the examples 1 and 2 of the priority application EP09075284 (filed on 1 Jul. 2009), both of which references are incorporated herein by reference (HV and LV correspond to LR and HR, respectively).

In short, starting with these selected individual plants with high or low EUE multiple cycles of self-crossing and selection for EUE were performed for the production of isogenic clones. Seeds of the low-EUE clone and the high-EUE clone were up-scaled. Stress testing in growth chambers and the greenhouse revealed that high-EUE plants show enhanced tolerance to ozone (4 days, 400 ppb) and heat (10 days, 45° C.) compared with control ("Simon") and low-EUE plants. In field trials of three subsequent years it could be demonstrated that high-EUE plants yield ~8% higher (kg seeds/ha) than control plants, while the low-EUE plants yield ~10% less than control plants. In fields with moderate drought stress, the line with the highest EUE had a 20% higher yield than that of the control, while the seed yield of the line with the highest respiration and lowest EUE dropped by 20% (Hauben et al., 2009).

Example 3—DNA Methylation Analysis and Transcriptome Analysis of Selected *B. napus* Plants 3.1 Analysis of Changes in DNA Methylation Status Methylation status, i.e. methylation of cytosine(s) in CG, CYG and CTH context (Y=C or T; H=A, T, or C) was investigated using Methylation sensitive Amplified Fragments Length Polymorphism (MSAP). For this, genomic DNA of *B. napus* plants of the selected plant lines of the cotyledon and of leaf 3 (just after appearance) was isolated according to the standard chloroform isoamylic alcohol protocol and was subsequently analyzed by DNA gel blot optionally after digestion with cytosine methylation sensitive restriction endonucleases, essentially as described in Hauben et al., 2009 and Matthes et al., 2001, Theor Appl Genet 102: p971-979, incorporated herein by reference. Sequences of the adapters and primers used are indicated in table 1 and in the sequence listing.

3.1.1 CG Methylome

To investigate changes in cytosine methylation state in CG sequence context, amplified fragments were scored according to the digestibility by the isochizomers HpaII and MspI of methylated inner cytosine residue within the 5'-C$\underline{C}$GG-3' restriction site, for either cotyledons or leaves. HpaII and Msp1 are isochizomers that recognize the same restriction site (5'-CCGG-3'). MspI does not cut if external cytosine is methylated, whereas HpaII fails to cut if internal cytosine is methylated and cuts poorly if external cytosine is methylated. The following Primers Enzyme Combinations (PECs) were used to survey the CG methylome: MH18M47; MH18M50; MH21M57; MH34HA67; MH76HA67; MH84HA67 (resulting in a total of 626 markers).

3.1.2 CYG Methylome

To investigate changes in cytosine methylation state in CYG context, the amplified fragments were scored according to the sensitivity of the isochizomers HpaII and MspI to methylated outer cytosine residue in 5'-$\underline{C}$CGG-3' restriction site (FIG. 1) and to the sensitivity of AluI to methylated cytosines residue within the 5'-AGCTG-3' restriction site (FIG. 2), for either cotyledons or leaves. The following PECs were used to survey the CYG methylome (Y stands for C and T):

CcG: MH18M47; MH18M50; MH21M57; MH84HA67; MH76HA67; MH34HA67 (66 markers);

CtG: E33A67, E33A70, E33A71 (397 markers);

resulting in a total of 463 markers for the CYG methylome.

3.1.3 CTH Methylome

To investigate changes in cytosine methylation state in CTH context, the amplified fragments were scored according to the sensitivity of AluI to methylated cytosines residue within the 5'-AGCTH-3' restriction site. The following PECs were run to survey the CTH methylome (H stands for A, T and C):

CTA: E33A37, E33A40, E33A41 (546 markers);

CTC: E33A47, E33A50, E33A51 (448 markers);

CTT: E33A88, E33A89, E33A94 (484 markers);

resulting in a total of 1475 markers for the CTH methylome.

TABLE 1

MSAP adapters and primers

| Application/name | sequence (5'-3') | SEQ ID NO | used after |
|---|---|---|---|
| Restriction/Ligation | | | |
| *AluI adapters* | | | |
| AluI adaptor A | GTTCTCAGGACTCATC | 1 | |
| AluI adapter B | GATGAGTCCTGAGAAC | 2 | |
| *EcoR1 adapters* | | | |
| EcoR1 adapter A | CTCGTAGACTGCGTACC | 3 | |
| EcoR1 adapter B | AATTGGTACGCAGTCTAC | 4 | |
| *HaeIII adapters* | | | |
| HaeIII adapter A | CTCAGGACTCATCGTC | 5 | |
| HaeIII adapter B | GACGATGAGTCCTGAG | 6 | |
| *Msp1/HpaII adapters* | | | |
| MH adapter A | CTCGACTGCGTACA | 7 | |
| MH adapter B | CGTGTACGCAGTC | 8 | |
| *Mse1 adapter* | | | |
| Mse1 adapter A | GACGATGAGTCCTGAG | 9 | |
| Mse1 adapter B | TACTCAGGACTCAT | 10 | |
| Preamplification (pa) | | | |
| *+1 AluI selective primers* | | | |
| A1 | GATGAGTCCTGAGAACCTA | 11 | |
| A2 | GATGAGTCCTGAGAACCTC | 12 | |
| A3 | GATGAGTCCTGAGAACCTG | 13 | |
| A4 | GATGAGTCCTGAGAACCTT | 14 | |
| *+1 EcoR1 selective primer* | | | |
| E1 | GACTGCGTACCAATTCA | 15 | |
| *+0 HaeIII selective primer* | | | |
| HA0 | GACGATGTGTCCTGAGCC | 16 | |
| *+1 Msp1/HpaII selective primers* | | | |
| MH1 | GACTGCGTACACGGA | 17 | |
| MH2 | GACTGCGTACACGGC | 18 | |
| MH3 | GACTGCGTACACGGG | 19 | |
| MH4 | GACTGCGTACACGGT | 20 | |
| *+1 Mse1 selective primer* | | | |
| M2 | GATGAGTCCTGAGTAAC | 21 | |
| Selective amplification | | | |
| *+3 AluI selective primers* | | | |
| A37 | GATGAGTCCTGAGAACCTACG | 22 | A1 pa |
| A40 | GATGAGTCCTGAGAACCTAGC | 23 | A1 pa |
| A41 | GATGAGTCCTGAGAACCTAGG | 24 | A1 pa |
| A47 | GATGAGTCCTGAGAACCTCAA | 25 | A2 pa |
| A50 | GATGAGTCCTGAGAACCTCAT | 26 | A2 pa |
| A51 | ATGAGTCCTGAGAACCTC | 27 | A2 pa |

TABLE 1-continued

MSAP adapters and primers

| Application/name | sequence (5'-3') | SEQ ID NO | used after |
|---|---|---|---|
| A67 | GATGAGTCCTGAGAACCTCA GCA | 28 | A3 pa |
| A70 | GATGAGTCCTGAGAACCTGCT | 29 | A3 pa |
| A71 | GATGAGTCCTGAGAACCTGGA | 30 | A3 pa |
| A88 | GATGAGTCCTGAGAACCTTGC | 31 | A4 pa |
| A89 | GATGAGTCCTGAGAACCTTGG | 32 | A4 pa |
| A94 | GATGAGTCCTGAGAACCTTTT | 33 | A4 pa |
| +3 EcoR1 selective primer | | | |
| E33 | GACTGCGTACCAATTCAAG | 34 | |
| +3 HaeIII selective primer | | | |
| HA67 | GACGATGTGTCCTGAGCCGCA | 35 | |
| +3 Msp1/HpaII selective primers | | | |
| MH18 | GACTGCGTACACGGCT | 36 | MH2 pa |
| MH21 | GACTGCGTACACGGGG | 37 | MH3 pa |
| MH34 | GACTGCGTACACGGAAT | 38 | MH1 pa |
| MH76 | GACTGCGTACACGGGTC | 39 | MH3 pa |
| MH84 | GACTGCGTACACGGTCC | 40 | MH4 pa |
| +3 Mse1 selective primers | | | |
| M47 | GATGAGTCCTGAGTAACAA | 41 | |
| M50 | GATGAGTCCTGAGTAACAT | 42 | |
| M57 | GATGAGTCCTGAGTAACGG | 43 | |

3.1.4 Analysis of Epigenetic Similarity

All scored amplified fragments from the MSAP displays were computed with NTSYS using the UPGMA method in order to survey the epigenetic similarity of the lines (FIG. 1).

The similarity coefficient indicates that, with regard to the CG sequence context, the selected lines are epigenetically similar whatever the development stage is (either cotyledons or leaves). However, with regard to non-CG sequences, the selected isogenic lines appear dissimilar. It was found that the divergence between the selected lines increases from cotyledons to leaves in CYG and CTH sequence contexts. The poor performing lines LV80 and LV82 are epigenetically similar. The high vigor-like line "Crashed" shifts from high to low vigor epigenetic similarity from cotyledons to leaves. The good performing lines HV76 and HV77 are epigenetically similar and Simon is dissimilar from its derivates.

3.2 Analysis of Changes in DNA Transcription Status

Changes in gene expression from cotyledon to leave stage were investigated using cDNA-AFLP, which was essentially performed as described in Vuylsteke et al. (2007; incorporated herein by reference). Briefly, total RNA of the selected plant lines of the cotyledon and 3th leave stage was extracted using the RNeasy Plant Mini Kit (QIAGEN) and reverse transcribed using the SMART™ cDNA Library Construction Kit (Clontech). The following PECs were used: E31M61, E32M47, E32M50, E32M51, E32M62, E33M50, E33M60, E33M62, E36M47, E43M4855, E46M5041, E46M59.

All scored amplified fragments from the cDNA-AFLP displays were computed with NTSYS using the UPGMA method in order to survey the transcript similarity of the lines (FIG. 2).

It was found that the divergence between the selected lines increases from cotyledons to leaves. The poor performing lines LV80 and LV82 are epigenetically similar. The high vigor-like line "Crashed" is dissimilar to all selected lines at leaves stage. The good performing line HV76 and Simon are closed and similar to HV77 which is still distinct from them.

3.3 Correlation Between Methylome and Transcriptome

The correlation between the percentage of occurrence of the no changes and changes in the various methylation patterns and the transcriptome of the selected plant lines from cotyledon to the 3th leaf stage in respect of the performance of the lines was calculated using R software under Spearman's p coefficient correlation. Spearman correlation analysis grouped changes (i.e. (de novo) methylation and demethylation) and no changes (unchan) in cytosine methylation and expression into three clades, with respect to the performance of the lines (low to high vigour), as is indicated in table 2 and visualized in a heat map (FIG.

3). The first clade (I) displays a non-specific pattern in changes and no changes in cytosine methylation and expression. The second clade (II) represents changes and no changes in cytosine methylation and expression highly occurring in the poor-performing lines while the third clade (III) reflects changes and no changes in cytosine methylation and expression highly occurring in the high-performing lines, i.e. this clade represents epigenetic features characteristic for high energy use efficiency.

TABLE 2

Percentage occurrence of epigenetic features in selected *B. napus* lines

|   | % per context | LV80 | LV82 | CRASHED | SIMON | HV76 | HV77 |
|---|---|---|---|---|---|---|---|
| c | mCTG_Gain | 8.23 | 4.66 | 6.53 | 9.48 | 5.67 | 5.42 |
|   | mCG_Lost | 3.97 | 3.68 | 3.71 | 4.24 | 3.72 | 2.66 |
|   | CTA_Unchan | 53.41 | 50.00 | 53.10 | 52.49 | 48.00 | 51.63 |
|   | mCTC_Lost | 6.33 | 5.73 | 4.85 | 8.05 | 5.63 | 6.62 |
|   | mCCG_Unchan | 56.36 | 54.55 | 48.21 | 61.40 | 45.00 | 48.28 |
|   | unExp_Unchan | 50.79 | 49.68 | 43.59 | 49.89 | 48.72 | 48.28 |
|   | Exp_Decrease | 19.89 | 20.32 | 22.81 | 22.47 | 21.85 | 19.83 |
| II | mCTA_Lost | 9.89 | 14.10 | 13.05 | 17.10 | 13.33 | 13.02 |
|   | Exp_Increase | 27.41 | 28.39 | 31.56 | 25.62 | 26.98 | 29.63 |
|   | CTC_Unchan | 52.51 | 55.30 | 56.38 | 54.03 | 56.01 | 54.41 |
|   | mCCG_Gain | 25.45 | 27.27 | 32.14 | 17.54 | 21.67 | 17.24 |
|   | mCG_Unchan | 6.20 | 6.37 | 5.94 | 4.99 | 5.71 | 5.07 |
|   | mCTA_Gain | 5.71 | 4.19 | 5.09 | 3.80 | 4.00 | 3.90 |
|   | mCTG_Unchan | 31.96 | 30.12 | 36.50 | 26.47 | 30.45 | 28.92 |
|   | mCTT_Unchan | 30.99 | 34.33 | 26.95 | 22.93 | 24.34 | 28.57 |
|   | mCTC_Unchan | 36.94 | 34.10 | 33.42 | 31.95 | 32.74 | 33.58 |
|   | CTG_Unchan | 53.48 | 55.28 | 50.74 | 52.61 | 53.13 | 54.82 |
|   | mCTA_Unchan | 30.99 | 31.72 | 28.76 | 26.60 | 34.67 | 31.45 |
| III | Exp_Unchan | 1.90 | 1.61 | 2.04 | 2.02 | 2.45 | 2.26 |
|   | CTT_Unchan | 53.05 | 52.49 | 54.14 | 53.41 | 56.09 | 53.16 |
|   | mCTT_Gain | 5.40 | 4.48 | 9.22 | 12.20 | 5.73 | 7.03 |
|   | CCG_Unchan | 0.00 | 0.00 | 1.79 | 0.00 | 1.67 | 3.45 |
|   | CG_Unchan | 89.08 | 88.73 | 88.86 | 88.78 | 88.83 | 90.10 |
|   | mCTC_Gain | 4.22 | 4.87 | 5.36 | 5.97 | 5.63 | 5.39 |
|   | mCG_Gain | 0.74 | 1.23 | 1.49 | 2.00 | 1.74 | 2.17 |
|   | mCTG_Lost | 6.33 | 9.94 | 6.23 | 11.44 | 10.75 | 10.84 |
|   | mCTT_Lost | 10.56 | 8.71 | 9.69 | 11.46 | 13.84 | 11.24 |
|   | mCCG_Lost | 18.18 | 18.18 | 17.86 | 21.05 | 31.67 | 31.03 |

Figure 4:
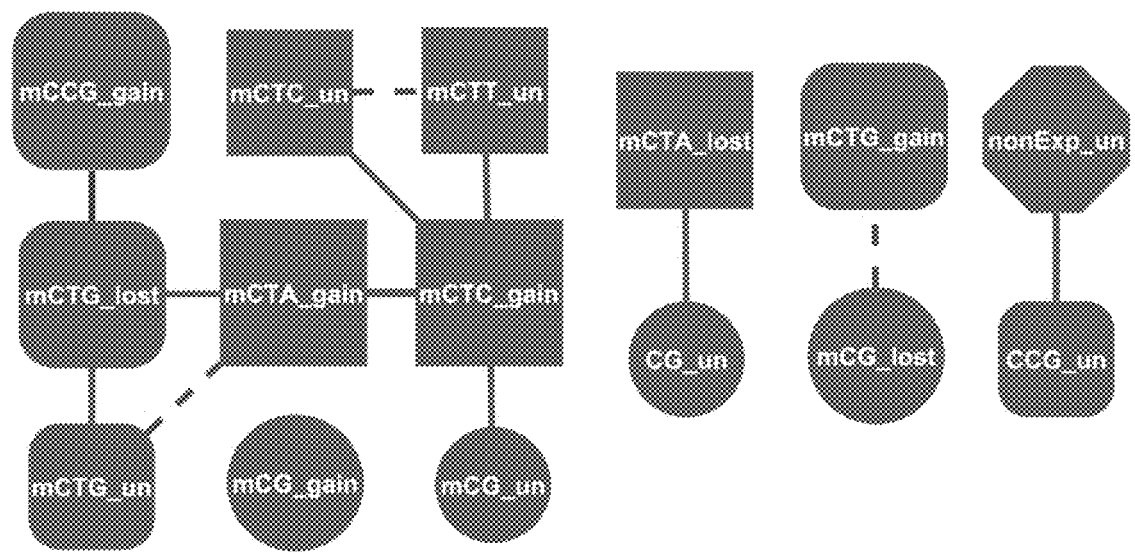
FIG. 4: Schematic representation of the significant correlations between methylation and expression profiles.

The strength and significance of the established correlations was determined by permutation analysis at p<0.05 under Spearman rank correlation with GraphPadPrism software. Changes and no changes in cytosine methylation state and expression were strongly related in either an increasing or decreasing relationship respectively for Spearman's correlation coefficient $0.8 \leq \rho \leq 1$ or $-1 \leq \rho \leq -0.8$ (Table 3, FIG. 4).

TABLE 3

| Variable 1 | Variable 2 | ρ | p-value |
|---|---|---|---|
| mCG_gain | mCG_unchan | −0.8857 | 0.0333 |
| mCG_gain | mCTA_gain | −0.8857 | 0.0333 |
| mCG_lost | mCTG_gain | 0.8857 | 0.0333 |
| mCG_unchan | mCTC_gain | −0.8857 | 0.0333 |
| CG_unchan | mCTA_lost | −0.8857 | 0.0333 |
| mCTG_lost | mCTG_unchan | −0.9429 | 0.0167 |
| mCTG_lost | mCCG_gain | −0.8857 | 0.0333 |
| mCTG_lost | mCTA_gain | −0.9429 | 0.0167 |
| mCTG_unchan | mCTA_gain | 0.8857 | 0.0333 |
| CCG_unchang | nonExp_unchan | −0.8804 | 0.0333 |
| mCTA_gain | mCTC_gain | −0.8857 | 0.0333 |
| mCTC_gain | mCTC_unchan | −0.9429 | 0.0167 |
| mCTC_gain | mCTT_unchan | −0.8857 | 0.0333 |
| mCTC_unchan | mCTT_unchan | 0.9429 | 0.0167 |

3.4 Correlation Between DNA Methylation Signature and Seed Yield Vigor

Figure 5:
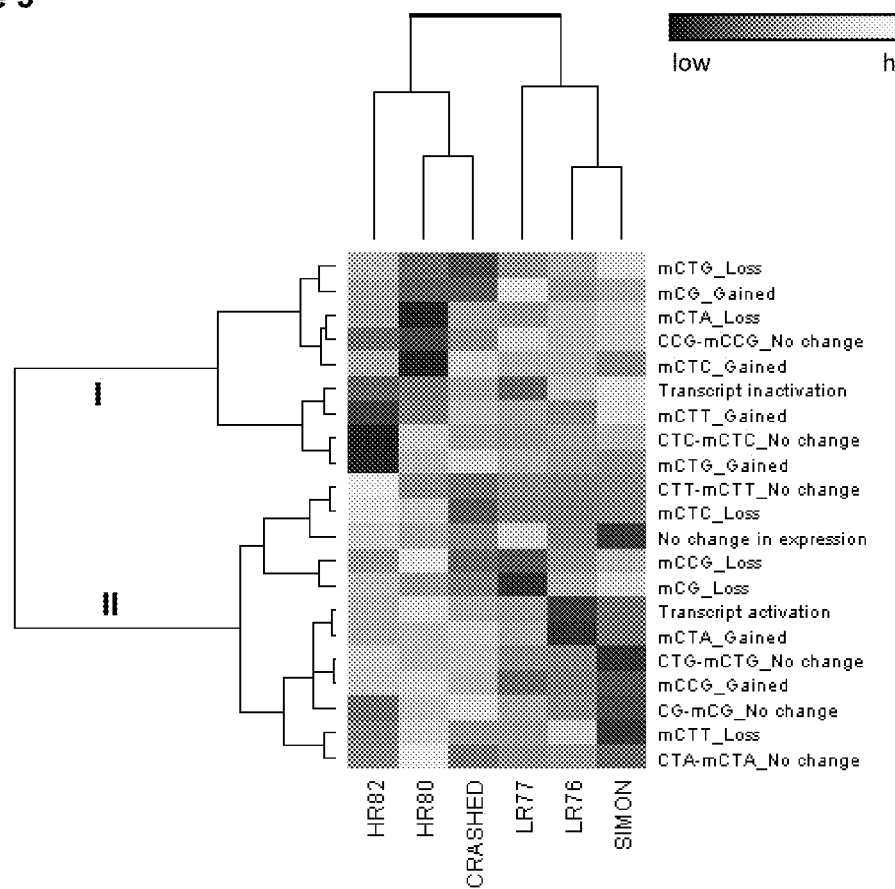
FIG. 5: Heatmap (A) and corresponding two-way hierarchical clustering under Pearson's coefficient of similarity (B) of changes and no changes in DNA methylation and expression from cotyledons to leaves in respect of the vigor/EUE of the lines based on a selection of the markers which were polymorphic at the cotyledon stage. HR (high respiring) and LR (low respiring) correspond to low vigor (LV) and high vigor (HV) respectively. Clade I (I) and clade II (II) represents features characteristic for a high EUE and for a low EUE respectively.
Figure 5:
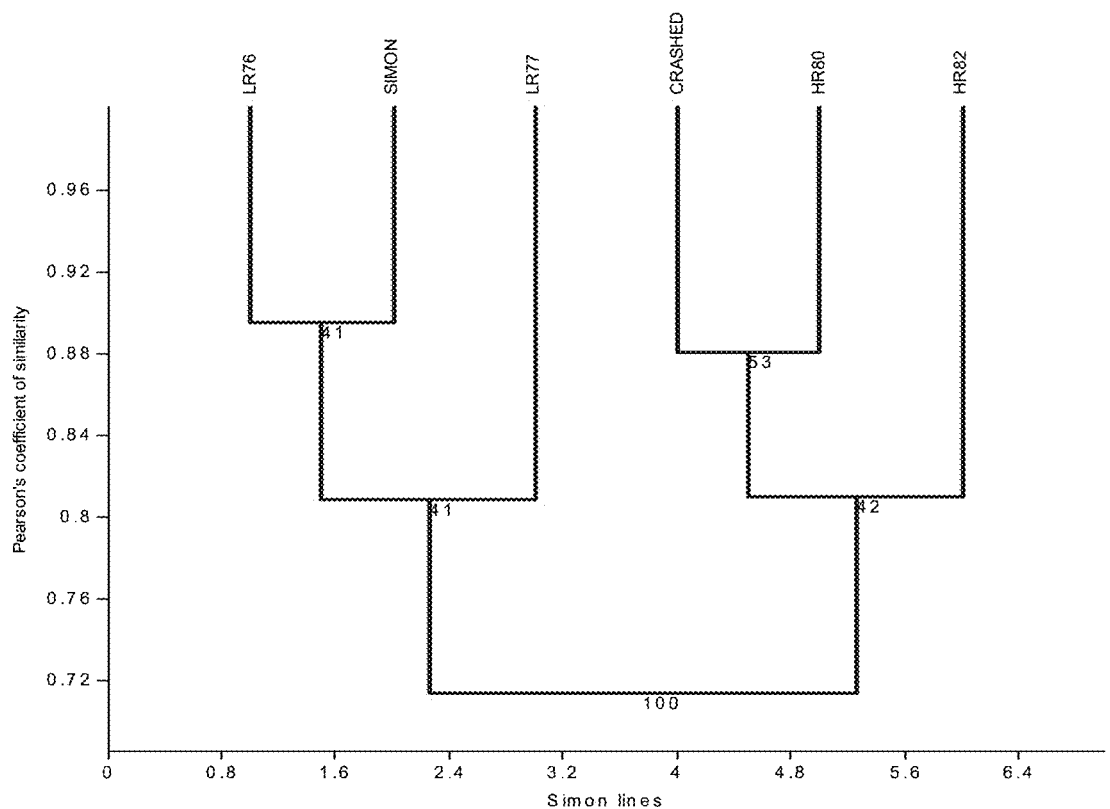

To further investigate the correlation between specific DNA methylation and gene expression profiles with respect to the energy use efficiency parameters of subclones cv. Simon, polymorphic MSAP and cDNA-AFLP markers between cotyledon and leaf developmental stage were first selected and the dataset was subsequently restricted to cotyledon polymorphic markers. This resulted to a selection of 397 from the total of 626 markers representing gain and loss of DNA methylation at CG, CCG, CTG, CTA, CTT and CTC sequence context, as well as activation and inactivation of transcript from cotyledon to leaf. This selection of markers enabled us to address how early changes in DNA methylation and gene expression evolved from cotyledon to leaf and was the basis of a two-way hierarchical clustering under Pearson's coefficient of similarity to identify energy use efficiency-DNA methylation and gene expression signatures, as represented in FIG. 5 and table 4 (representing raw data of heatmap of FIG. 5A).

Figure 6:
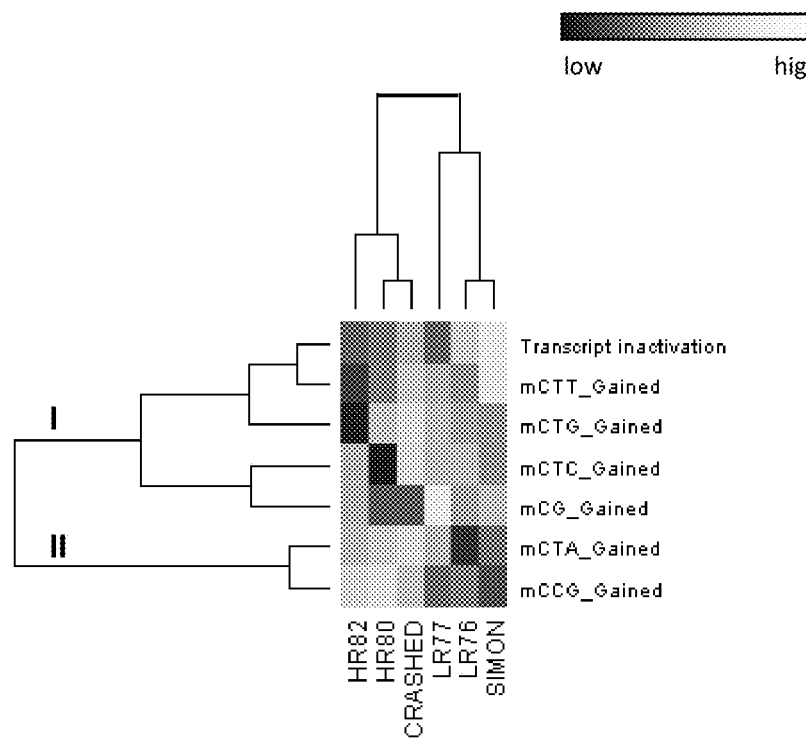
FIG. 6: Heatmap (A) and corresponding two-way hierarchical clustering under Pearson's coefficient of similarity (B) of gain in DNA methylation and decrease in expression from cotyledons to leaves in respect of the vigor/EUE of the lines based on a selection of the markers which were polymorphic at the cotyledon stage. HR (high respiring) and LR (low respiring) correspond to low vigor (LV) and high vigor (HV), respectively. Clade I (I) and clade II (II) represents features characteristic for a high EUE and for a low EUE respectively.
Figure 6:
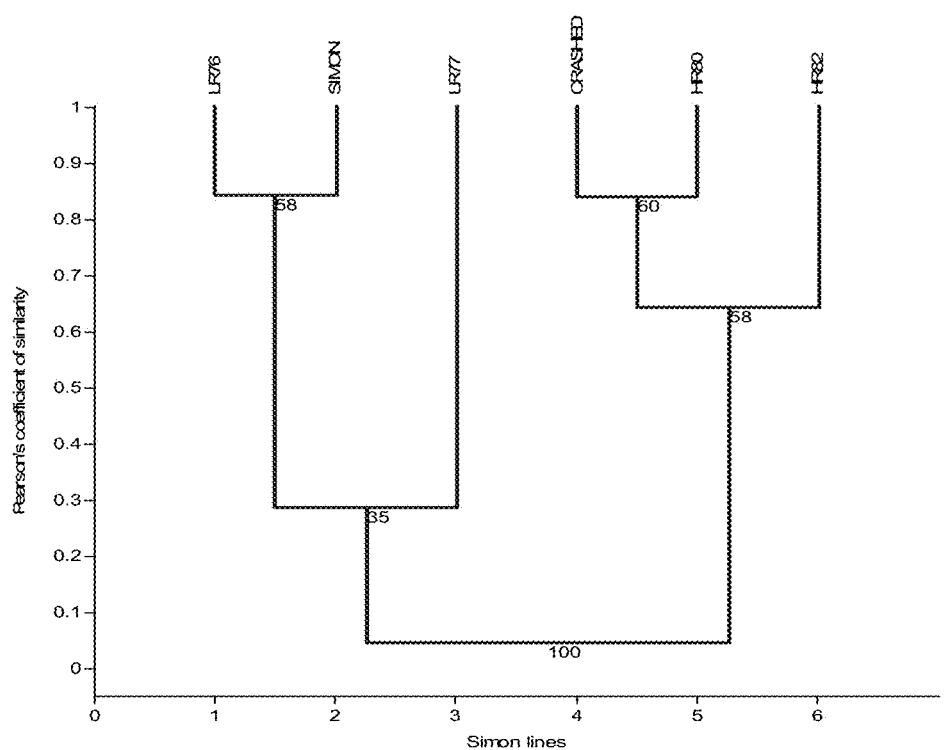

To avoid redundancy in the information, the analysis was further restricted to markers associated with gain of DNA methylation and transcript inactivation from cotyledon to leaf, as represented in FIG. 6 and table 5 (representing raw data of heatmap of FIG. 6A). When analyzing the relationship within the vigor lines, it becomes apparent that cluster formation is associated with gain of DNA methylation and gene inactivation (FIG. 6). A specific gain-in-DNA methylation and transcript inactivation profile clustered the low vigor lines LV80 and LV82 and Crashed apart from the high vigor lines HV76, HV77 and Simon (p<0.01, FIG. 6). A coincident trend of higher DNA methylation at CG, CTG, CTT and CTC sites in HV76 and HV77 was observed from cotyledon to leaf. Alternatively, gain of cytosine methylation tend to occur in a less extent in the low vigor lines LV80 and LV82, except at CCG and CTA sites where methylcytosines tend to be greatly enriched when compared with the high vigor lines and Simon. These results illustrate the relationship between vigor and seed yield performance and the cumulative abundance of methylcytosines at specific sequence context from cotyledon to leaf in respect to the mitochondrial respiration rate and energy use efficiency of the selected lines.

Besides these changes in DNA methylation that were related to energy use efficiency parameters, cluster analysis showed that transcript inactivation tend to occur in a greater extent in Simon, HV76, and "Crashed" as compared with the other subclones from cotyledon to leaf (FIG. 6). Interestingly, "Crashed" which aligned with the low vigor lines LV80 and LV82 shared a significant trend in gain of DNA methylation at specific non-CG sites with the low respiring lines (FIG. 6). Gain of DNA methylation in CTA and CCG sites tends to occur in "Crashed" as in the low vigor lines LV80 and LV82. When compared to the high vigor lines HV76 and HV77, gain of CG methylation tend to be weakly established in "Crashed". These results demonstrate the possibility to select specific DNA methylation profiles that represent the vigor and seed yield performance of physiologically selected genotypes for their mitochondrial respiration rate and energy content. Furthermore, they highlight the relative importance of gain of CG methylation from cotyledon to leaf under extended high vigor (low-respiration) selection.

TABLE 4

Percentage occurrence of epigenetic features in selected *B. napus* lines based on selection of markers that are polymorphic at the cotyledon stage.

|  | LV82 | LV80 | CRASHED | HV77 | HV76 | SIMON |
| --- | --- | --- | --- | --- | --- | --- |
| mCTG_Loss | 32.43 | 20.93 | 17.07 | 27.27 | 31.11 | 40.00 |
| mCG_Gained | 16.67 | 0.00 | 0.00 | 33.33 | 14.29 | 20.00 |
| mCTA_Loss | 27.50 | 12.20 | 27.78 | 26.97 | 31.88 | 34.62 |
| CCG-mCCG_No change | 38.46 | 25.00 | 50.00 | 75.00 | 64.29 | 72.73 |
| mCTC_Gained | 21.21 | 8.89 | 25.58 | 22.45 | 22.22 | 18.75 |
| Transcript inactivation | 21.88 | 26.47 | 36.36 | 22.22 | 42.37 | 52.24 |
| mCTT_Gained | 9.72 | 18.42 | 27.85 | 24.39 | 20.51 | 34.18 |
| CTC-mCTC_No change | 45.45 | 62.22 | 58.14 | 57.14 | 57.78 | 60.42 |
| mCTG_Gained | 2.70 | 16.28 | 19.51 | 15.91 | 13.33 | 12.50 |
| CTT-mCTT_No change | 70.83 | 53.95 | 50.63 | 53.66 | 52.56 | 53.16 |
| mCTC_Loss | 33.33 | 28.89 | 16.28 | 20.41 | 20.00 | 20.83 |
| mCCG_Loss | 15.38 | 25.00 | 10.00 | 8.33 | 14.29 | 18.18 |
| mCG_Loss | 33.33 | 25.00 | 16.67 | 0.00 | 28.57 | 40.00 |
| Transcript activation | 10.94 | 13.24 | 10.61 | 9.52 | 5.08 | 7.46 |
| mCTA_Gained | 13.75 | 14.63 | 15.56 | 13.48 | 7.25 | 10.26 |
| CTG-mCTG_No change | 64.86 | 62.79 | 63.41 | 56.82 | 55.56 | 47.50 |
| mCCG_Gained | 46.15 | 50.00 | 40.00 | 16.67 | 21.43 | 9.09 |
| CG-mCG_No change | 50.00 | 75.00 | 83.33 | 66.67 | 57.14 | 40.00 |
| mCTT_Loss | 19.44 | 27.63 | 21.52 | 21.95 | 26.92 | 12.66 |

TABLE 5

Percentage occurrence of epigenetic features representing a gain in selected *B. napus* lines based on selection of markers that are polymorphic at the cotyledon stage.

|  | LV82 | LV80 | CRASHED | HV77 | HV76 | SIMON |
| --- | --- | --- | --- | --- | --- | --- |
| Transcript inactivation | 21.88 | 26.47 | 36.36 | 22.22 | 42.37 | 52.24 |
| mCTT_Gained | 9.72 | 18.42 | 27.85 | 24.39 | 20.51 | 34.18 |
| mCTG_Gained | 2.70 | 16.28 | 19.51 | 15.91 | 13.33 | 12.50 |
| mCTC_Gained | 22.22 | 22.45 | 18.75 | 8.89 | 21.21 | 25.58 |
| mCG_Gained | 16.67 | 0.00 | 0.00 | 33.33 | 14.29 | 20.00 |
| mCTA_Gained | 13.75 | 14.63 | 15.56 | 13.48 | 7.25 | 10.26 |
| mCCG_Gained | 46.15 | 50.00 | 40.00 | 16.67 | 21.43 | 9.09 |

The invention claimed is:

1. A method for preparing a *Brassica* plant with a high energy use efficiency from a collection of plants from the same species or variety which are genetically uniform plants comprising the steps of:
   a) providing a population consisting of a plurality of individual *Brassica* plants which are genetically uniform;
   b) obtaining a genomic DNA sample from individual plants of said population at least at a first and a second developmental stage in a manner which allows further cultivation of said sampled individual plants, wherein said first developmental stage is the cotyledon stage and said second developmental stage is the third leaf stage of said plant;
   c) determining of each of said individual plants a methylation profile of said genomic DNA obtained at said at least two stages;
   d) determining the epigenetic features of each of said individual plants by evaluating the changes in DNA methylation profile between said first and said second stage; and
   e) identifying and selecting at least one plant which has a high relative occurrence of at least five epigenetic features characteristic for high energy use efficiency when compared to the average occurrence of said epigenetic features in other plants of said population, wherein said epigenetic features are selected from: mCTC-gain, mCG-gain, mCTG-loss, mCTT-loss, and mCCG-loss.

2. The method of claim 1, wherein said at least one plant has a high relative occurrence of at least six epigenetic features that are characteristic for high energy use efficiency when compared to the average occurrence of said epigenetic features in said population, wherein said epigenetic features characteristic for high energy use efficiency are selected from mCTG-loss, mCG-gain, mCTA-loss, no change in CCG-mCCG, mCTC-gain, mCTT-gain, no change in CTC-mCTC or mCTG-gain, wherein said epigenetic features have been determined based on markers that are polymorphic at said first stage.

3. The method of claim 1, wherein said at least one plant has a high relative occurrence of at least six epigenetic features that are characteristic for high energy use efficiency when compared the average occurrence of said epigenetic features in said population, wherein said epigenetic features characteristic for high energy use efficiency are selected from mCTG-loss, mCG-gain, mCTA-loss, no change in CCG-mCCG, mCTC-gain or mCTT-gain, wherein said epigenetic features have been determined based on markers that are polymorphic at said first stage.

4. The method of claim 1, wherein said selected at least one plant is further crossed with another plant.

5. A method of producing a *Brassica* hybrid plant or hybrid seed comprising
   a) crossing an inbred *Brassica* plant with a high energy use efficiency from a population consisting of *Brassica* plants which are genetically uniform plants, with another inbred *Brassica* plant; and
   b) isolating hybrid seed of the cross,
   wherein the inbred *Brassica* plant with a high energy use efficiency has a high relative occurrence of at least five epigenetic features characteristic for high energy use efficiency when compared to the average occurrence of said epigenetic features in other plants of said population, wherein said epigenetic features are selected from: mCTC-gain, mCG-gain, mCTG-loss, mCTT-loss, and mCCG-loss.

6. The method of claim 5, further comprising c) growing hybrid plants from the hybrid seed.

7. A method for preparing a differential DNA methylation profile, comprising
   a) obtaining a genomic DNA sample from individual plants of a population consisting of a plurality of individual *Brassica* plants which are genetically uniform at least at a first and a second developmental stage in a manner which allows further cultivation of said sampled individual plants, wherein said first developmental stage is the cotyledon stage and said second developmental stage is the third leaf stage of said plant;

b) preparing a methylation profile each individual plant at said at least two stages;

c) determining the epigenetic features of each of said individual plants by evaluating the changes in DNA methylation profile between said first and said second stage; and d) preparing a differential DNA methylation profile of at least one plant which has a high relative occurrence of at least five epigenetic features characteristic for high energy use efficiency when compared to the average occurrence of said epigenetic features in other plants of said population, wherein said epigenetic features are selected from: mCTC-gain, mCG-gain, mCTG-loss, mCTT-loss, and mCCG-loss.

8. The method of claim 7, wherein said at least one plant has a high relative occurrence of at least six epigenetic features that are characteristic for high energy use efficiency when compared to the average occurrence of said epigenetic features in said population, wherein said epigenetic features characteristic for high energy use efficiency are selected from mCTG-loss, mCG-gain, mCTA-loss, no change in CCG-mCCG, mCTC-gain, mCTT-gain, no change in CTC-mCTC or mCTG-gain, wherein said epigenetic features have been determined based on markers that are polymorphic at said first stage.

9. The method of claim 7, wherein said at least one plant has a high relative occurrence of at least six epigenetic features that are characteristic for high energy use efficiency when compared the average occurrence of said epigenetic features in said population, wherein said epigenetic features characteristic for high energy use efficiency are selected from mCTG-loss, mCG-gain, mCTA-loss, no change in CCG-mCCG, mCTC-gain or mCTT-gain, wherein said epigenetic features have been determined based on markers that are polymorphic at said first stage.

* * * * *

SEQUENCE LISTING

<160> NUMBER OF SEQ ID NOS: 43

<210> SEQ ID NO 1
<211> LENGTH: 16
<212> TYPE: DNA
<213> ORGANISM: Artificial Sequence
<220> FEATURE:
<223> OTHER INFORMATION: adapter

<400> SEQUENCE: 1
gttctcagga ctcatc

-continued

```
<210> SEQ ID NO 2
<211> LENGTH: 16
<212> TYPE: DNA
<213> ORGANISM: Artificial Sequence
<220> FEATURE:
<223> OTHER INFORMATION: adapter

<400> SEQUENCE: 2
gatgagtcct gagaac                                                     16

<210> SEQ ID NO 3
<211> LENGTH: 17
<212> TYPE: DNA
<213> ORGANISM: Artificial Sequence
<220> FEATURE:
<223> OTHER INFORMATION: adapter

<400> SEQUENCE: 3
ctcgtagact gcgtacc                                                    17

<210> SEQ ID NO 4
<211> LENGTH: 18
<212> TYPE: DNA
<213> ORGANISM: Artificial Sequence
<220> FEATURE:
<223> OTHER INFORMATION: adapter

<400> SEQUENCE: 4
aattggtacg cagtctac                                                   18

<210> SEQ ID NO 5
<211> LENGTH: 16
<212> TYPE: DNA
<213> ORGANISM: Artificial Sequence
<220> FEATURE:
<223> OTHER INFORMATION: adapter

<400> SEQUENCE: 5
ctcaggactc atcgtc                                                     16

<210> SEQ ID NO 6
<211> LENGTH: 16
<212> TYPE: DNA
<213> ORGANISM: Artificial Sequence
<220> FEATURE:
<223> OTHER INFORMATION: adapter

<400> SEQUENCE: 6
gacgatgagt cctgag                                                     16

<210> SEQ ID NO 7
<211> LENGTH: 14
<212> TYPE: DNA
<213> ORGANISM: Artificial Sequence
<220> FEATURE:
<223> OTHER INFORMATION: adapter

<400> SEQUENCE: 7
ctcgactgcg taca                                                       14

<210> SEQ ID NO 8
<211> LENGTH: 13
<212> TYPE: DNA
<213> ORGANISM: Artificial Sequence
<220> FEATURE:
```

<223> OTHER INFORMATION: adapter

<400> SEQUENCE: 8
cgtgtacgca gtc                                              13

<210> SEQ ID NO 9
<211> LENGTH: 16
<212> TYPE: DNA
<213> ORGANISM: Artificial Sequence
<220> FEATURE:
<223> OTHER INFORMATION: adapter

<400> SEQUENCE: 9
gacgatgagt cctgag                                           16

<210> SEQ ID NO 10
<211> LENGTH: 14
<212> TYPE: DNA
<213> ORGANISM: Artificial Sequence
<220> FEATURE:
<223> OTHER INFORMATION: adapter

<400> SEQUENCE: 10
tactcaggac tcat                                             14

<210> SEQ ID NO 11
<211> LENGTH: 19
<212> TYPE: DNA
<213> ORGANISM: Artificial Sequence
<220> FEATURE:
<223> OTHER INFORMATION: preamplification primer

<400> SEQUENCE: 11
gatgagtcct gagaaccta                                        19

<210> SEQ ID NO 12
<211> LENGTH: 19
<212> TYPE: DNA
<213> ORGANISM: Artificial Sequence
<220> FEATURE:
<223> OTHER INFORMATION: preamplification primer

<400> SEQUENCE: 12
gatgagtcct gagaacctc                                        19

<210> SEQ ID NO 13
<211> LENGTH: 19
<212> TYPE: DNA
<213> ORGANISM: Artificial Sequence
<220> FEATURE:
<223> OTHER INFORMATION: preamplification primer

<400> SEQUENCE: 13
gatgagtcct gagaaccta                                        19

<210> SEQ ID NO 14
<211> LENGTH: 19
<212> TYPE: DNA
<213> ORGANISM: Artificial Sequence
<220> FEATURE:
<223> OTHER INFORMATION: preamplification primer

<400> SEQUENCE: 14
gatgagtcct gagaacctt                                        19

```
<210> SEQ ID NO 15
<211> LENGTH: 17
<212> TYPE: DNA
<213> ORGANISM: Artificial Sequence
<220> FEATURE:
<223> OTHER INFORMATION: preamplification primer

<400> SEQUENCE: 15
gactgcgtac caattca                                                      17

<210> SEQ ID NO 16
<211> LENGTH: 18
<212> TYPE: DNA
<213> ORGANISM: Artificial Sequence
<220> FEATURE:
<223> OTHER INFORMATION: preamplification primer

<400> SEQUENCE: 16
gacgatgtgt cctgagcc                                                     18

<210> SEQ ID NO 17
<211> LENGTH: 15
<212> TYPE: DNA
<213> ORGANISM: Artificial Sequence
<220> FEATURE:
<223> OTHER INFORMATION: preamplification primer

<400> SEQUENCE: 17
gactgcgtac acgga                                                        15

<210> SEQ ID NO 18
<211> LENGTH: 15
<212> TYPE: DNA
<213> ORGANISM: Artificial Sequence
<220> FEATURE:
<223> OTHER INFORMATION: preamplification primer

<400> SEQUENCE: 18
gactgcgtac acggc                                                        15

<210> SEQ ID NO 19
<211> LENGTH: 15
<212> TYPE: DNA
<213> ORGANISM: Artificial Sequence
<220> FEATURE:
<223> OTHER INFORMATION: preamplification primer

<400> SEQUENCE: 19
gactgcgtac acggg                                                        15

<210> SEQ ID NO 20
<211> LENGTH: 15
<212> TYPE: DNA
<213> ORGANISM: Artificial Sequence
<220> FEATURE:
<223> OTHER INFORMATION: preamplification primer

<400> SEQUENCE: 20
gactgcgtac acggt                                                        15

<210> SEQ ID NO 21
<211> LENGTH: 17
<212> TYPE: DNA
<213> ORGANISM: Artificial Sequence
<220> FEATURE:
<223> OTHER INFORMATION: preamplification primer
```

<400> SEQUENCE: 21
gatgagtcct gagtaac					17

<210> SEQ ID NO 22
<211> LENGTH: 21
<212> TYPE: DNA
<213> ORGANISM: Artificial Sequence
<220> FEATURE:
<223> OTHER INFORMATION: primer

<400> SEQUENCE: 22
gatgagtcct gagaacctac g					21

<210> SEQ ID NO 23
<211> LENGTH: 21
<212> TYPE: DNA
<213> ORGANISM: Artificial Sequence
<220> FEATURE:
<223> OTHER INFORMATION: primer

<400> SEQUENCE: 23
gatgagtcct gagaacctag c					21

<210> SEQ ID NO 24
<211> LENGTH: 21
<212> TYPE: DNA
<213> ORGANISM: Artificial Sequence
<220> FEATURE:
<223> OTHER INFORMATION: primer

<400> SEQUENCE: 24
gatgagtcct gagaacctag g					21

<210> SEQ ID NO 25
<211> LENGTH: 21
<212> TYPE: DNA
<213> ORGANISM: Artificial Sequence
<220> FEATURE:
<223> OTHER INFORMATION: primer

<400> SEQUENCE: 25
gatgagtcct gagaacctca a					21

<210> SEQ ID NO 26
<211> LENGTH: 21
<212> TYPE: DNA
<213> ORGANISM: Artificial Sequence
<220> FEATURE:
<223> OTHER INFORMATION: primer

<400> SEQUENCE: 26
gatgagtcct gagaacctca t					21

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
atgagtcctg agaacctcca					20

<210> SEQ ID NO 28
<211> LENGTH: 21

```
<212> TYPE: DNA
<213> ORGANISM: Artificial Sequence
<220> FEATURE:
<223> OTHER INFORMATION: primer

<400> SEQUENCE: 28
gatgagtcct gagaacctgc a                                              21

<210> SEQ ID NO 29
<211> LENGTH: 21
<212> TYPE: DNA
<213> ORGANISM: Artificial Sequence
<220> FEATURE:
<223> OTHER INFORMATION: primer

<400> SEQUENCE: 29
gatgagtcct gagaacctgc t                                              21

<210> SEQ ID NO 30
<211> LENGTH: 21
<212> TYPE: DNA
<213> ORGANISM: Artificial Sequence
<220> FEATURE:
<223> OTHER INFORMATION: primer

<400> SEQUENCE: 30
gatgagtcct gagaacctgg a                                              21

<210> SEQ ID NO 31
<211> LENGTH: 21
<212> TYPE: DNA
<213> ORGANISM: Artificial Sequence
<220> FEATURE:
<223> OTHER INFORMATION: primer

<400> SEQUENCE: 31
gatgagtcct gagaaccttg c                                              21

<210> SEQ ID NO 32
<211> LENGTH: 21
<212> TYPE: DNA
<213> ORGANISM: Artificial Sequence
<220> FEATURE:
<223> OTHER INFORMATION: primer

<400> SEQUENCE: 32
gatgagtcct gagaaccttg g                                              21

<210> SEQ ID NO 33
<211> LENGTH: 21
<212> TYPE: DNA
<213> ORGANISM: Artificial Sequence
<220> FEATURE:
<223> OTHER INFORMATION: primer

<400> SEQUENCE: 33
gatgagtcct gagaaccttt t                                              21

<210> SEQ ID NO 34
<211> LENGTH: 19
<212> TYPE: DNA
<213> ORGANISM: Artificial Sequence
<220> FEATURE:
<223> OTHER INFORMATION: primer

<400> SEQUENCE: 34
```

-continued

```
gactgcgtac caattcaag                                                19

<210> SEQ ID NO 35
<211> LENGTH: 21
<212> TYPE: DNA
<213> ORGANISM: Artificial Sequence
<220> FEATURE:
<223> OTHER INFORMATION: primer

<400> SEQUENCE: 35
gacgatgtgt cctgagccgc a                                             21

<210> SEQ ID NO 36
<211> LENGTH: 16
<212> TYPE: DNA
<213> ORGANISM: Artificial Sequence
<220> FEATURE:
<223> OTHER INFORMATION: primer

<400> SEQUENCE: 36
gactgcgtac acggct                                                   16

<210> SEQ ID NO 37
<211> LENGTH: 16
<212> TYPE: DNA
<213> ORGANISM: Artificial Sequence
<220> FEATURE:
<223> OTHER INFORMATION: primer

<400> SEQUENCE: 37
gactgcgtac acgggg                                                   16

<210> SEQ ID NO 38
<211> LENGTH: 17
<212> TYPE: DNA
<213> ORGANISM: Artificial Sequence
<220> FEATURE:
<223> OTHER INFORMATION: primer

<400> SEQUENCE: 38
gactgcgtac acggaat                                                  17

<210> SEQ ID NO 39
<211> LENGTH: 17
<212> TYPE: DNA
<213> ORGANISM: Artificial Sequence
<220> FEATURE:
<223> OTHER INFORMATION: primer

<400> SEQUENCE: 39
gactgcgtac acgggtc                                                  17

<210> SEQ ID NO 40
<211> LENGTH: 17
<212> TYPE: DNA
<213> ORGANISM: Artificial Sequence
<220> FEATURE:
<223> OTHER INFORMATION: primer

<400> SEQUENCE: 40
gactgcgtac acggtcc                                                  17

<210> SEQ ID NO 41
<211> LENGTH: 19
<212> TYPE: DNA
<213> ORGANISM: Artificial Sequence
```

```
<220> FEATURE:
<223> OTHER INFORMATION: primer

<400> SEQUENCE: 41
gatgagtcct gagtaacaa                                                19

<210> SEQ ID NO 42
<211> LENGTH: 19
<212> TYPE: DNA
<213> ORGANISM: Artificial Sequence
<220> FEATURE:
<223> OTHER INFORMATION: primer

<400> SEQUENCE: 42
gatgagtcct gagtaacat                                                19

<210> SEQ ID NO 43
<211> LENGTH: 19
<212> TYPE: DNA
<213> ORGANISM: Artificial Sequence
<220> FEATURE:
<223> OTHER INFORMATION: primer

<400> SEQUENCE: 43
gatgagtcct gagtaacgg                                                19
```